United States Patent
Badry et al.

(10) Patent No.: US 7,511,487 B2
(45) Date of Patent: Mar. 31, 2009

(54) LOGGING METHOD FOR DETERMINING CHARACTERISTIC OF FLUID IN A DOWNHOLE MEASUREMENT REGION

(75) Inventors: Robert Badry, Calgary (CA); Charles Flaum, Beijing (CN); Robert Kleinberg, Cambridge, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 0 days.

(21) Appl. No.: 11/679,574

(22) Filed: Feb. 27, 2007

(65) Prior Publication Data

US 2008/0204013 A1    Aug. 28, 2008

(51) Int. Cl.
   *G01V 3/00*    (2006.01)
(52) U.S. Cl. .................................... 324/303
(58) Field of Classification Search ................... 324/303
   See application file for complete search history.

(56) References Cited

U.S. PATENT DOCUMENTS

| | | | |
|---|---|---|---|
| 3,528,000 | A | 9/1970 | Schwede |
| 5,023,551 | A | 6/1991 | Kleinberg et al. |
| 5,055,787 | A | 10/1991 | Kleinberg et al. |
| 5,291,137 | A | 3/1994 | Freedman |
| 5,486,762 | A | 1/1996 | Freedman et al. |
| 6,005,389 | A | 12/1999 | Prammer |
| 6,107,796 | A | 8/2000 | Prammer |
| 6,111,408 | A | 8/2000 | Blades et al. |
| 6,111,409 | A | 8/2000 | Edwards et al. |
| 6,229,308 | B1 * | 5/2001 | Freedman ............... 324/303 |
| 6,346,813 | B1 * | 2/2002 | Kleinberg ............... 324/303 |
| 6,630,357 | B2 * | 10/2003 | Mirotchnik et al. ...... 436/173 |
| 6,765,380 | B2 * | 7/2004 | Freedman ............... 324/303 |
| 6,825,657 | B2 * | 11/2004 | Kleinberg et al. ....... 324/303 |
| 6,841,996 | B2 | 1/2005 | Madio et al. |
| 6,859,032 | B2 * | 2/2005 | Heaton et al. ........... 324/303 |
| 6,859,033 | B2 * | 2/2005 | Speier .................... 324/303 |
| 6,891,369 | B2 * | 5/2005 | Hurlimann et al. ...... 324/303 |
| 6,952,096 | B2 * | 10/2005 | Freedman ............... 324/303 |
| 7,091,719 | B2 * | 8/2006 | Freedman ............... 324/303 |
| 7,309,983 | B2 * | 12/2007 | Freedman ............... 324/303 |

OTHER PUBLICATIONS

Bryan et al., Viscosity Prediction for Crude Oils and Crude Oil Emulsions Using Low Field NMR, SPE 77329, 2002, pp. 1-11.

(Continued)

*Primary Examiner*—Dixomara Vargas
(74) *Attorney, Agent, or Firm*—James McAleenan; Jody DeStefanis; Vincent Loccisano

(57) ABSTRACT

For use in logging downhole in an earth borehole, a method for determining a characteristic of oil, includes: providing and determining the viscosity of a plurality of crude oil samples; performing test measurements, using a predetermined operating mode, on media including the crude oil samples to obtain test data; applying a test processing procedure to the test data to obtain an output test parameter relating to the test data and the predetermined operating mode; deriving, for the plurality of crude oil samples, a correlation relating the output test parameter to the viscosities of the crude oil samples; performing downhole measurements in the measurement region with a logging device, operated with substantially the predetermined operating mode, to obtain logging data, and applying a measurement processing procedure to the logging data to obtain an output logging parameter; and determining the oil characteristic using the output logging parameter and the correlation.

30 Claims, 14 Drawing Sheets

OTHER PUBLICATIONS

Bryan et al., Oil Viscosity Predictions From Low-Field NMR Measurements, SPE Reservoir Evaluation and Engineering, Feb. 2005, pp. 44-52.

Freedman et al., Fluid Characterization using Nuclear Magnetic Resonance Logging, Petrophysics 45, 2004, pp. 241-250.

Heaton et al., Applications of a New-Generation NMR Wireline Logging Tool, SPE 77400, 2002, pp. 1-10.

Hirasaki et al., NMR properties of petroleum reservoir fluids, Magnetic Resonance Imaging, 21, 2003, pp. 269-277.

Kleinberg et al., NMR Properties of Reservoir Fluids, Log Analyst, Nov.-Dec. 1996, pp. 20-32.

Kleinberg et al., Review: NMR Detection and Characterization of Hydrocarbons in Subsurface Earth Formations, in Blumich et al. eds., Spatially Resolved Magnetic Resonance: Methods and Applications in Materials Science, Agriculture and Biomedicine, Wiley-VCH, 1998, pp. 555-573.

Lo et al., Mixing Rules and Correlations of NMR Relaxation Time with Viscosity, Diffusivity, and Gas/Oil Ration of Methane/Hydrocarbon Mixtures, SPE 77264, SPE Journal 7(1), Mar. 2002, pp. 24-34.

Microtchnik et al., Low-Field NMR Method for Bitumen Sands Characterization: A New Approach, SPE Reservoir Evaluation & Engineering, 4 (2), Apr. 2001, pp. 88-96.

Morriss et al., Hydrocarbon Saturation and Viscosity Estimation from NMR Logging in the Belridge Diatomite, Paper C, SPWLA 35th Annual Logging Symposium, Jun. 1994, pp. 1-24.

Seccombe et al., Ranking Oil Viscosity in Heavy Oil Reservoirs, SPWLA 46th Annual Logging Sumposium, Jun. 2005, pp. 1-12.

Vinegar, Whole Core Analysis by 13C NMR, SPE 19590, SPE Formation Evaluation, Jun. 1991, 183-212.

Watson et al., Characterization of Petroleum Fractions, Industrial and Engineering Chemistry 27, 1935, pp. 1460-1464.

Borgia et al., Examples of marginal resolution of NMR relaxation peaks using UPEN and diagnostics, Magentic Resonance Imaging 19, 2001, pp. 473-475.

Brown et al., NMR Logging Tool Development: Laboratory Studies of Tight Gas Sands and Artificial Porous Media, SPE/DOE 10813, SPE Unconventional Gas Recovery Symposium, May 1982, pp. 16-18.

Buthod, Crud Oil Properties and Condensate Properties and Correlations, H.B. Bradley et al., eds, Petroleum Engineering Handbook, Society of Petroleum Engineers, Richardson TX, 1992, pp. 21-1-21-20.

Canas et al., Viscous Oil Dynamics Evaluation for Better Fluid Sampling, SPE/PS-CIM/CHOA 97767, SPE International Thermal Operations and Heavy Oil Symposium, Calgary, Alberta, Canada, Nov. 2005, pp. 1-11.

Carr et al., Effects of Diffusion on Free Precession in Nuclear Magnetic Resonance Experiements, Physical Review 94, 1954, pp. 630-638.

Morriss et al., Operating Guide for the Combinable Magnetic Resonance Tool, The Log Analyst, vol. 37, No. 6, 1996, pp. 53-60.

Hurlimann et al., Diffusion-relaxation distribution functions of sedimentary rocks in different saturation states, Magnetic Resonance Imaging 21, 2003, pp. 305-310.

Hurlimann et al., Diffusion-Editing: New NMR Measurement of Saturation and Pore Geometry, SPWLA 43rd Annual Logging Symposium, 2002, 1-14.

Meiboom et al., Modified Spin-Echo Method for Measuring Nuclear Relaxation Times, Review of Scientific Instruments 29, 1958, pp. 688-691.

Sezginer et al., Very Rapid Simultaneous Measurement of Nuclear Magnetic Resonance Spin-Lattis Relaxation Time and Spin-Spin Relaxation Time, Journal of Magnetic Resonance, 92, 1991, pp. 504-527.

Mckeon et al., An Improved NMR Tool Design for Faster Logging, Transactions of the SPWLA 40th Annual Logging Symposium, Paper CC, 1999, pp. 1-14.

Latorraca et al., Heavy Oil Viscosity Determination Using NMR Logs, SPWLA 40th Annual Logging Symposium, Paper PPP, 1999, pp. 1-11.

Depavia et al., A Next-Generation Wireline NMR Logging Tool, SPE 84482, Society of Petroleum Engineers, 2003, pp. 1-7.

Kleinberg et al., Tapered Cutoffs for Magnetic Resonance Bound Water Volume, Society of Petroleum Engineers Paper 38737, 1997, pp. 197-202.

Freedman et al., Field Applications of a New Nuclear Magnetic Resonance Fluid Characterization Method, SPE Reservoir Evaluation and Engineering, Dec. 2002, pp. 455-464.

Freedman et al., A New NMR Method of Fluid Characterization in Reservoir Rocks: Experimental Confirmation and Simulation Results, SPE 63214, SPE Annual Technical Conference and Exhibition, Oct. 2000, pp. 1-15.

Kleinberg, Nuclear Magnetic Resonance, in P.-z. Wong, ed., Experimental Methods in the Physical Sciences, vol. 35, Methods in the Physics of Porous Media, Academic Press, 1999, pp. 337-384.

Winkler et al., The Limits of Fluid Property Correlations Used In NMR Well Logging An Experimental Study of Reservoir Fluids At Reservoir Conditions, SPWLA 45th Annual Logging Symposium, Paper DD, Jun. 2004, pp. 1-13.

Kleinberg, Well Logging, Encyclopedia of Nuclear Magnetic Resonance, John Wiley & Sons, 1996, pp. 4960-4969.

Freedman et al., Measurement of Total NMR Porosity Adds New Value to NMR Logging, SPWLA 38th Annual Logging Symposium, Jun. 1997, Paper OO, pp. 1-14.

* cited by examiner

TABLE 1

| | WL/LWD[1] | $(T_E)_{min}$(ms) | G(G/cm) | $G_{max} \cdot (T_E)_{min}$ (G·s/cm) |
|---|---|---|---|---|
| #1 | WL | 0.2 | 20[2] | 0.004 |
| #2 | WL | 0.2 | 20[2] | 0.004 |
| #3 | WL | 0.45 | 12-43 | 0.02 |
| #4 | LWD | 0.8 | 3 | 0.002 |
| #5 | WL | 0.6 | 18 | 0.01 |
| #6 | WL | 0.6 | 17-21 | 0.01 |
| #7 | LWD | 0.5 | 14 | 0.007 |
| #8 | WL | 0.6 | 17-34 | 0.02 |

LOGGING METHOD FOR DETERMINING CHARACTERISTIC OF FLUID IN A DOWNHOLE MEASUREMENT REGION

FIELD OF THE INVENTION

This invention relates to logging downhole in an earth borehole and, more particularly, to a logging method for determining a characteristic of a fluid, especially oil, that may be present in a downhole measurement region.

BACKGROUND OF THE INVENTION

Immense heavy oil reservoirs exist in many parts of the world. Heavy oil endowments are hundreds of billions of barrels in some nations. However, much of the heavy oil in place can be uneconomical to produce depending on factors such as conventional oil price, distance to markets, and refining complexity. One of the primary determinants of oil value is its viscosity.

Heavy oil reservoirs may contain several grades of oil. For example, a reservoir might be composed of stacked porous beds separated by impermeable layers. Each bed can contain oil with properties different from the oils in beds above and below. It is believed that fluid properties can vary even within a single bed, so that, for example, viscosity increases from the top to the bottom of the bed.

Producers seeking to select their best prospects generally want to locate the beds containing oil with the lowest viscosity, among other desirable properties. Borehole logging tools generally are the most accurate and cost-effective means of determining properties of fluids found in subsurface geological formations. One method that has been found suitable for this purpose is formation sampling. In a form of this technique a borehole logging tool (e.g. the Schlumberger "MDT™" tool) extracts fluid from the formation, stores it in a sample bottle, and conveys the bottle to the surface. The sample is then typically transferred to another bottle for shipment to a fluids analysis laboratory. Fluids laboratories are capable of determining a variety of physical and chemical properties, including viscosity.

Despite the success of downhole fluid sampling, a number of factors limit the effectiveness of this technique, as described below. (1) Only a relatively small number of oil samples can be obtained in each descent of the tool into the borehole, typically only six or twelve samples. (2) It is time consuming to obtain a good sample, typically an hour or more. This is a disadvantage due to the very high cost of operating drilling rigs. (3) Transporting the samples to a laboratory and having them characterized there can take weeks, which can impede the production schedule. (4) Sample integrity can be jeopardized by temperature and/or pressure changes associated with uphole handling, and by the transfer of samples to and from transportation cylinders. (5) It is not practical to obtain samples of oils with viscosity greater than several thousand centipoise [see, for example, J. A. Cañas, S. Low, N. Adur and V. Teixeira, "Viscous Oil Dynamics Evaluation For Better Fluid Sampling", SPE/PS-CIM/CHOA 97767, SPE International Thermal Operations and Heavy Oil Symposium, Calgary, Alberta, Canada, 1-3 Nov. 2005].

Some of the listed limitations can be mitigated by making measurements of fluids such as oils within the fluid sampling tool itself. One such measurement is nuclear magnetic resonance (NMR) [see, for example, U.S. Pat. Nos. 3,528,000; 6,107,796; 6,111,408; 6,111,409; 6,346,813; 6,825,657; 6,841,996; and U.S. Pat. No. 6,891,369]. In some approaches, fluids in a flowline of fluid sampling tool are subjected to NMR measurements while downhole. Techniques of the present invention apply, inter alia, to NMR measurements in fluid sampling tools, as well as to various other types of measurements, as will be described.

Nuclear magnetic resonance logging of earth formations surrounding a borehole is another way of estimating the viscosity of heavy oils. Although NMR estimates of viscosity are widely regarded as less accurate than viscometer measurements made in fluids laboratories, NMR well logs have the following advantages: (1) Depth-continuous log data is frequently possible to obtain; (2) When it is necessary to collect data at stations, the NMR station stops are typically much shorter than fluid sampling station stops; (3) The data is available at the well site, either during the drilling process (for logging-while-drilling) or shortly afterwards (for wireline); (4) Sample integrity is not an issue since the measurements are made on oil in situ; (5) NMR well logs are very economical compared to downhole fluid sampling; and (6) NMR can measure viscosity up to at least one million centipoise. Techniques of the present invention apply, inter alia, to wireline and to logging-while-drilling NMR tools.

Examples of Some Typical NMR Measurements

As part of the background hereof, it is useful to review some NMR pulse sequences commonly in use in borehole logging tools, such as to obtain longitudinal relaxation time, $T_1$, transverse relaxing time $T_2$, diffusion constant, D, and/or distributions and/or cross-distributions of the foregoing. The following notation applies to exemplary sequences described herein. Typical, but non-limiting, exemplary values of the pulse sequence parameters are in parentheses:

$N_E$=number of echoes (3000)
$N_{EL}$=number of echoes (long wait time) (3000)
$N_{ES}$=number of echoes (short wait time) (30)
N=number of repetitions (10)
$N_L$=number of repetitions (long wait time) (1)
$N_S$=number of repetitions (short wait time) (10)
$T_E$=echo spacing (1 ms)
$T_{Ei}$=variable echo spacing (0.1-10 ms), i=1, 2, 3 . . .
W=wait time (1 s)
$W_i$=variable wait time (0.001-10 s)
$W_L$=wait time (long) (1 s)
$W_S$=wait time (short) (20 ms)
90°=90° pulse
180°=180° pulse Sequence (1) below is interpreted as follows, with sequences (2)-(4) interpreted analogously.

CPMG Sequence: Wait a time W; apply a 90° pulse; wait a time $T_E/2$ (measured from the middle of the 90° pulse); apply a 180° pulse; wait a time $T_E/2$ (measured from the middle of the 180° pulse); acquire an echo; repeat the echo acquisition sequence $N_E$ times; repeat the entire sequence N times.

Carr-Purcell-Meiboom-Gill (CPMG; $T_2$) (see FIG. 1):

$$N \times [W + 90° + N_E \times (T_E/2 + 180° + T_E/2 + \text{echo})] \quad (1)$$

When the wait time W is varied, the pulse sequence is the so-called Saturation Recovery/Carr-Purcell-Meiboom-Gill (SR/CPMG) pulse sequence, which is listed next, for the measurement of T1 and T2 simultaneously [see e.g. U.S. Pat. No. 5,032,551; and A. Sezginer, R. L. Kleinberg, M. Fukuhara, and L. L. Latour, "Very Rapid Simultaneous Measurement Of Nuclear Magnetic Resonance Spin-Lattice Relaxation Time And Spin-Spin Relaxation Time", Journal of Magnetic Resonance, 92, 504 (1991)].

Saturation Recovery CPMG (SR/CPMG; $T_1$, $T_2$) (again, see FIG. 1):

$$\text{For } i=1 \text{ to } N, \, [W_i+90°+N_E \times (T_E/2+180°+T_E/2+\text{echo})] \quad (2)$$

Enhanced Precision Mode (EPM; $T_2$) (see FIG. 2):

$$N_L \times [W_L+90°+N_{EL} \times (T_E/2+180°+T_E/2+\text{echo})]+N_S \times [W_S+90°+N_{ES} \times (T_E/2+180°+T_E/2+\text{echo})] \quad (3)$$

FIG. 2 illustrates the timing of a prior art so-called Enhanced Precision Mode (EPM). After a long wait time $W_L=W1$, a single long CPMG sequence is acquired. Then, a series of short CPMG sequences is acquired with short wait time $W_S=W2$ between each. The short sequences improve the precision of the early-time magnetization decay [see D. McKeon, C. Cao Minh, R. Freedman, R. Harris, D. Willis, D. Davies, G. Gubelin, R. Oldigs, and M. Hürlimann, "An Improved NMR Tool Design For Faster Logging", Transactions of the SPWLA 40th Annual Logging Symposium, paper CC (1999)].

Diffusion Editing (DE; D, $T_2$) (see FIG. 3):

$$\text{For } i=1 \text{ to } N, \, [W+90°+2 \times (T_{Ei}/2+180°+T_{Ei}/2+\text{echo})+ N_E \times (T_E/2+180°+T_E/2+\text{echo})] \quad (4)$$

FIG. 3 illustrates the timing of a prior art so-called diffusion editing (DE) pulse sequence to measure D-T2 distribution functions [see M. D. Hurlimann, L. Venkataramanan, C. Flaum, P. Speier, C. Karmonik, R. Freedman, and N. Heaton, "Diffusion-Editing: New NMR Measurement Of Saturation And Pore Geometry", SPWLA 43rd Annual Logging Symposium, 2-5 Jun. 2002].

Examples of NMR Measurement Results

An important output of the NMR measurement of crude oil, or of crude oil mixed with water in rock, is the transverse relaxation time distribution, $m_i(T_2)$. It is defined in terms of the echo amplitude decay, $M(t)$ $$M(t) = \sum_i m_i(T_{2i}) \cdot \exp\left[-\frac{t}{T_{2i}}\right] \quad (5)$$

Crude oils have very broad distributions of relaxation times. FIG. 4 illustrates transverse relaxation time distributions of crude oils. The $T_2$-distributions for bulk oil samples from the Belridge field, Calif., are plotted in order of increasing viscosity, from top left to bottom right. Sample number logarithmic mean $T_2$ ($T_{2,log}$) and measured viscosity (in centipoise) are shown for each example. [see C. E. Morriss, R. Freedman, C. Straley, M. Johnston, H. J. Vinegar, and P. N. Tutunjian, "Hydrocarbon Saturation And Viscosity Estimation From NMR Logging In The Belridge Diatomite", Paper C, SPWLA 35th Annual Logging Symposium, 19-22 Jun. 1994]. For certain purposes, the entire distribution may be displayed and manipulated. For other purposes, the information in the distribution may be characterized by its logarithmic mean, or geometric mean, $$T_{2gm} = T_{2LM} = 10^{[\Sigma_i m_i \log_{10}(T_{2i})]/\Sigma_i m_i} \quad (6)$$

Another type of NMR measurement is the $T_1$ distribution J. A. Brown, L. F. Brown, J. A. Jackson, J. V. Milewski, and B. J. Travis, "NMR Logging Tool Dvelopment: Laboratory Studies Of Tight Gas Sands And Atificial Porous Media", SPE/DOE 10813, SPE Unconventional Gas Recovery Symposium, 16-18 May 1982 defined analogously to the $T_2$ distribution. Its logarithmic mean (or geometric mean) is $$T_{1gm} = T_{1LM} = 10^{[\Sigma_i m_i \log_{10}(T_{1i})]/\Sigma_i m_i} \quad (7)$$

The span of a relaxation time distribution is limited by the data available. NMR instruments have dead times, during which no data are available. For presently deployed borehole tools, this dead time is $T_E$, the echo spacing. No components of the crude oil relaxation that have decayed significantly during $T_E$ can appear in the relaxation time distribution. FIG. 5 illustrates the relaxation time distributions of seven hypothetical, but realistic, crude oils. In this Figure, which does not represent the characteristics of any particular laboratory instrument or logging tool, $T_2$ components shorter than 0.2 ms are invisible (dotted curves). One effect of the invisible components is that $T_{2gm}$ (or $T_{1gm}$) appears to be longer than if the entire distribution were available to be included in Eqn (6) (or Eqn (7)).

NMR tools also measure hydrogen index, HI, which is the ratio of the signal amplitude from the earth formation to the signal amplitude from a container of pure water that is at least as large as the entire volume sensed by the tool. NMR logging tools automatically correct for changes in sensitivity between shop calibration conditions and borehole measurement conditions.

Some laboratories measure relative hydrogen index of hydrocarbon, RHI [see, e.g., J. Bryan, A. Kantzas, and C. Bellehumeur, "Oil viscosity predictions from low field NMR measurements", SPE Reservoir Evaluation and Engineering, February 2005, 44-52], as $$RHI = \frac{\text{hydrocarbon amplitude/mass}}{\text{water amplitude/mass}} \quad (8)$$

where the oil and water are measured at the same temperature. The relationship between HI and RHI is $$HI = RHI \frac{\rho_h}{\rho_w} \quad (9)$$

where $\rho_h$ is the hydrocarbon density and $\rho_w$ is the water density.

Many low viscosity crude oils have hydrogen index values that are near to that of water [see, e.g., R. L. Kleinberg and H. J. Vinegar, "NMR properties of reservoir fluids", Log Analyst, November 1996, 20-32], i.e. HI≈1. Heavy oils can have HI<1 for two reasons. Firstly, the intrinsic hydrogen density of these oils can be less than that of water or light oils. Secondly, hydrogen that is present may be invisible to the NMR measurement, due to rapid magnetic relaxation of the hydrogen nuclei.

The concentration of hydrogen, [H], in moles/cm³, of a pure substance is $$[H] = \frac{n_H \cdot \rho}{MW} \quad (10)$$

where nH is the number of hydrogen atoms in the chemical formula of the substance, and ρ and MW are the density and molecular weight of the substance. A crude oil does not have a fixed composition. It may, however, be characterized by its average chemical composition CHX, which has a molecular weight MW=(12.011+X·1.0079). nH is given by the average ratio of hydrogen to carbon atoms, nH=H/C≡X, so the molar density of hydrogen is $$[H]_h = \frac{\rho_h \cdot X}{12.011 + X \cdot 1.0079} \qquad (11)$$

The molar density of hydrogen in water, $H_2O$, is $$[H]_w = \frac{\rho_w \cdot n_H}{MW} = 0.111 \, moles/cm^3 \qquad (12)$$

so the intrinsic hydrogen index of hydrocarbon crude oils as a function of H/C ratio is $$HI_i = \frac{1}{0.111 \, moles/cm^3} \cdot \frac{\rho_h \cdot X}{12.011 + X \cdot 1.0079} \qquad (13)$$

The H/C ratio of crude oils is variable. The end members are referred to as paraffinic (predominantly alkanes, X~2) and aromatic (substantial fraction of aromatic rings, X<2). The characterization factor K [see, e.g., K. M. Watson, E. F. Nelson, and G. B. Murphy, "Characterization of Petroleum Fractions", Industrial and Engineering Chemistry 27, 1460-1464 (1935)] is a convenient method of systematizing these compositional families. Predominantly paraffinic oils have K~12.5, while predominantly aromatic oils have K~10. H/C ratio has also been found to be correlated with API gravity (density). Using published data [see P. Buthod, "Crude Oil Properties and Condensate Properties and Correlations", in H. B. Bradley et al, eds, Petroleum Engineering Handbook, Society of Petroleum Engineers, Richardson Tex., 1992], the intrinsic hydrogen index can be predicted as a function of API gravity for K=11 and K=12 (see FIG. 6).

The intrinsic hydrogen index is the upper limit of the hydrogen detected by NMR. NMR amplitude measurements can fail to measure the intrinsic hydrogen index because, as noted above, part of the hydrogen signal decays during the dead time of the measurement. Because high viscosity is related to rapid signal decay, the apparent hydrogen index is most reduced for the highest viscosity oils. FIG. 7a shows laboratory measurements of NMR-visible relative hydrogen index as a function of viscosity for a group of Canadian heavy oils [see J. Bryan, A. Kantzas, and C. Bellehumeur, "Oil Viscosity Predictions From Low Field NMR Measurements", SPE Reservoir Evaluation and Engineering, February 2005, 44-52]. [See Bryan et al., 2005, supra].

The existing art includes, a number of NMR techniques for estimating the in situ viscosity of oil in subsurface geological formations. Oil is commingled with water and sometimes free gas in hydrocarbon bearing rocks. All three contribute to the NMR measurement. In order to estimate the properties of the oil phase, it is necessary to separate the oil contributions from the others. Once the oil signal is isolated, its NMR relaxation characteristics can be used to find the viscosity. Several NMR viscosity estimation methods have been described in the petrophysics literature, including the following:

(a) An early NMR method of measuring viscosity was to find the oil peak in the T1 or T2 distribution, compute a numerical characteristic of the oil peak such as the logarithmic mean T2, and relate that to viscosity with a standard viscosity correlation, e.g. that described in Kleinberg and Vinegar, 1996, supra. This method has been extended to 100,000 centipoise, see FIGS. 7b and 10.

(b) The so-called "missing signal method" [see H. J. Vinegar, P. N. Tutunjian, W. A. Edelstein, and P. B. Roemer, "Whole Core Analysis By 13C NMR", SPE Formation Evaluation, June 1991, 183-212] was developed in the Middle East [see R. L. Kleinberg and C. Flaum, "Review: NMR Detection And Characterization Of Hydrocarbons In Subsurface Earth Formations", in B. Blumich et al. eds., Spatially Resolved Magnetic Resonance: Methods and Applications in Materials Science, Agriculture and Biomedicine, Wiley-VCH (1998)] and Canada [see K. D. Mirotchnik, K. Allsopp, A. Kantzas, D. Curwen, and R. Badry, "Low-Field NMR Method For Bitumen Sands Characterization: A new Approach", SPE Reservoir Evaluation & Engineering, 4(2), 88-96 (April 2001), and J. Bryan, A. Kantzas, and C. Bellehumeur, "Viscosity Prediction For Crude Oils And Crude Oil Emulsions Using Low Field NMR", SPE 77329 (2002)]. Whereas relaxation time becomes less sensitive to viscosity as viscosity increases, the NMR signal from a given volume of oil (hydrogen index) decreases as viscosity increases, see FIGS. 7a and 7b. This is because, as viscosity increases, an increasing fraction of the hydrogen NMR signal decays within the instrumental dead time. This method is effective between several thousand centipoise and millions of centipoise.

(c) The so-called "Magnetic Resonance Fluids" ("MRF™") technique, of Schlumberger, separates oil, water, and free gas contributions. Data acquisition includes combinations of saturation recovery, CPMG, and diffusion editing pulse sequences, sequences similar to (2) and (4) above, using various values of TE and W. A data processing algorithm outputs the saturation of each fluid, and the oil viscosity [see N. J. Heaton, R. Freedman, C. Karmonik, R. Taherian, K. Walter, and L. DePavia, "Applications Of A New Generation NMR Wireline Logging Tool", SPE 77400, SPE Annual Technical Conference and Exhibition, 29 Sep.-2 Oct. 2002; and R. Freedman and N. Heaton, "Fluid Characterization Using Nuclear Magnetic Resonance Logging", Petrophysics, 45, 241-250 (2004)]. MRF (a trademark of Schlumberger) is available as a wireline station log and in a logging-while-drilling tool, and it is available as a continuous log. This method is applicable for oils with viscosity less than about 100 cp viscosity. See FIG. 8 for an example.

(d) The so-called diffusion editing technique uses the DE sequence of (4) above, repeated with various values of $T_{Ei}$ but with always the same value of $T_E$. A processing algorithm creates diffusion-relaxation maps [see Hurlimann et al., 2002, supra], which can be related to viscosity. However, this method works only for oils with viscosity less than about 100 cp viscosity. See FIG. 9 for an example.

It has been found that the most versatile method of estimating viscosity is to combine methods (a) and (b)—in other words to use both relaxation time information and missing signal information. One equation that has been proposed [see Bryan et al., 2002, supra] is the empirical equation:

$$\eta = \frac{\alpha}{(RHI)^\beta T_{2gm}} \qquad (14)$$

The constants α and β are selected to best fit a data set. For the data set referenced in Bryan et al., supra, α=1.15 and β=4.55 were found to be suitable.

Prior art methods for using NMR to estimate oil viscosity have limited application. Method (a) only works when oil and water are well separated in the relaxation time distribution. In heavy oil reservoirs, the irreducible water signal tends to coincide with the oil signal, and careful log analysis is needed to eliminate the influence of water. Failure to account for the water signal has compromised some viscosity estimations, such as that described in J. Seccombe, R. Akkurt, M. Smith, and R. J. M. Bonnie, "Ranking Oil Viscosity In Heavy Oil Reservoirs" SPWLA 46th Annual Logging Symposium, 26-29 Jun. 2005. Methods (c) and (d) are only suitable for limited ranges of viscosity, generally less than 100 cp.

SUMMARY OF THE INVENTION

It has not heretofore been recognized that methods (a) and (b) depend on the details of the NMR acquisition technique. The following acquisition parameters are among those found to influence relaxation time and hydrogen index measures of heavy oils:

Pulse Sequence: The pulse sequence most often used in laboratory measurements and borehole logging tools is CPMG. However, other sequences are sometimes used, including diffusion-edited sequences [see e.g. M. D. Hürlimann, M. Flaum, L. Venkataramanan, C. Flaum, R. Freedman, and G. J. Hirasaki, "Diffusion—Relaxation Distribution Functions Of Sedimentary Rocks in Different Saturation States", Magnetic Resonance Imaging 21, 305-310 (2003)], multi-wait methods [R. Freedman and C. E. Morriss, "Apparatus Including Multi-Wait Time Pulsed NMR Logging Method For Determining Accurate T2 Distributions And Accurate T1/T2 Ratios And Generating A More Accurate Output Record Using The Updated T2 Distributions And T1/T2 Ratios", U.S. Pat. No. 5,486,762 (1996)] and the enhanced precision mode (EPM) [McKeon et al., 1999, supra]. For a given heavy oil, each of these sequences will give different results for relaxation time and hydrogen index measures. For example, EPM tends to give higher values of RHI and lower values of $T_{2gm}$ than the simple CPMG does.

Echo Spacing TE: Various laboratory instruments and borehole logging tools use different values of echo spacing within their acquisition sequences. Table 1 shows the minimum CPMG echo spacings in use for various logging tools. Increasing the echo spacing decreases RHI and increases $T_{2gm}$ [see K. D. Mirotchnik, K. Allsopp, A. Kantzas, D. Curwen, and R. Badry, "Low-Field NMR Method For Bitumen Sands Characterization: A new Approach", SPE Reservoir Evaluation & Engineering, 4(2), 88-96 (April 2001)].

Signal to Noise Ratio S/N: The signal to noise ratio affects the measurement of the NMR properties of heavy oils. For example, when NMR data is analyzed with a processing algorithm using regularization to produce a relaxation time distribution [see R. Freedman, "Processing Method And Apparatus For Processing Spin Echo In-Phase And Quadrature Amplitudes From A Pulsed Nuclear Magnetism Tool And Producing New Output Data To Be Recorded On An Output Record", U.S. Pat. No. 5,291,137 (1994)], low S/N will result in broader T2 distributions. Signal to noise is affected by the inherent noise of the logging tool, and by the amount of stacking. To achieve stacked data, measurements over depth intervals must be commingled, reducing vertical resolution. Hence there is a trade-off between high S/N ratio and good vertical resolution.

Processing Algorithm: Each pulse sequence uses a different processing algorithm to find NMR measurement results. Moreover, a given pulse sequence can be processed in a variety of ways. For example, the CPMG sequence can be processed by the so-called Schlumberger method [Freedman, 1994, supra], the so-called NUMAR method [see M. G. Prammer, "Pulse Sequences And Interpretation Techniques For NMR Measurements", U.S. Pat. No. 6,005,389 (1999)], or the so-called UPEN method [see G. C. Borgia, R. J. S. Brown, and P. Fantazzini, "Examples Of Marginal Resolution Of NMR Relaxation Peaks Using UPEN And Diagnostics", Magnetic Resonance Imaging 19, 473-475 (2001)]. In general, given identical raw data inputs, these methods give different relaxation time and hydrogen index results when some signal is lost due to hydrogen relaxation within the dead time of the measurement.

An embodiment of the invention has application for use in logging downhole in an earth borehole. A method is set forth for determining a characteristic of oil that may be present in a downhole measurement region, including the following steps: providing a plurality of crude oil samples; determining the viscosities of the crude oil samples; performing test measurements, using a predetermined operating mode, on media including the crude oil samples to obtain test data; applying a test processing procedure to the test data to obtain an output test parameter relating to said test data and the predetermined operating mode; deriving, for the plurality of crude oil samples, a correlation relating the output test parameter to the viscosities of the crude oil samples; performing downhole measurements in the measurement region with a logging device, operated with substantially said predetermined operating mode, to obtain logging data, and applying a measurement processing procedure to the logging data to obtain an output logging parameter; and determining the oil characteristic using said output logging parameter and said correlation.

In a preferred embodiment, the characteristic of oil comprises the viscosity of oil in the measurement region. The characteristic of oil may also comprise, for example, the distribution of viscosities of crude oil components in the measurement region, oil volume in the measurement region, oil saturation in the measurement region, light oil volume and/or heavy oil volume in the measurement region, and/or light oil saturation and/or heavy oil saturation in the measurement region.

Also in a preferred embodiment of the invention, the test measurements are nuclear magnetic resonance test measurements, and the step of performing downhole measurements in the measurement region with a logging device comprises performing the downhole measurements in the measurement region with a nuclear magnetic resonance logging device. In a form of this embodiment, the step of performing test measurements comprises simulating measurements by the logging device used to perform downhole measurements. In another form of this embodiment, the step of performing test measurements comprises performing said measurements with the logging device used to perform downhole measurements.

In a form of a preferred embodiment of the invention, the step of performing nuclear magnetic resonance test measurements using a predetermined operating mode comprises performing the nuclear magnetic resonance test measurements using a predetermined pulse sequence with predetermined pulse sequence parameters. In another form of this embodiment, the step of performing nuclear magnetic resonance test measurements using predetermined operating mode comprises performing the nuclear magnetic resonance test measurements using a predetermined signal-to-noise ratio.

An embodiment of the invention further comprises the following steps: performing further test measurements, using a further operating mode, on media including said crude oil samples to obtain further test data; applying said test processing procedure to said further test data to obtain a further output test parameter relating to said test data and said predetermined operating mode; deriving, for said plurality of crude oil samples, a further correlation relating said further output test parameter to the viscosities of said crude oil samples; performing downhole measurements in the measurement region with a logging device, operated with substantially said further operating mode, to obtain further logging data, and applying said measurement processing procedure to said further logging data to obtain a further output logging parameter; and determining an oil characteristic using said further output logging parameter and said further correlation.

A further preferred embodiment of the invention is also applicable for use in logging downhole in an earth borehole. A method is set forth for determining a characteristic of oil that may be present in a downhole measurement region, including the following steps: providing a plurality of crude oil samples; determining the viscosities of the crude oil samples; performing magnetic resonance test measurements, using a plurality of operating modes, on media including the crude oil samples to obtain a corresponding plurality of sets of test data; applying a test processing procedure to each of the plurality of sets of test data to obtain a corresponding plurality of output test parameters relating to the respective plurality of operating modes; deriving, for the plurality of crude oil samples, a plurality of correlations, each of the correlations relating the plurality of output test parameters to the viscosities of the crude oil samples; performing downhole measurements in the measurement region with a nuclear magnetic resonance logging device, operated substantially with one of said plurality of operating modes, to obtain a set of logging data, and applying a measurement processing procedure to the logging data to obtain an output logging parameter; and determining the oil characteristic using the output logging parameter and a selected one of said plurality of correlations. In a form of this embodiment of the invention, the selected one of said correlations is the correlation that corresponds to said one of the plurality of operating modes. The characteristic of oil can comprise, for example, the viscosity of oil in the measurement region, or the distribution of viscosities of crude oil components in the measurement region. Also in a form of this embodiment, the step of performing nuclear magnetic resonance test measurements comprises simulating measurements by the nuclear magnetic resonance logging device used to perform downhole measurements, or performing said measurements with the nuclear magnetic resonance logging device used to perform downhole measurements. Also, in a form of this embodiment, the step of performing nuclear magnetic resonance test measurements using a plurality of operating modes comprises performing said nuclear magnetic resonance test measurements using a plurality of different pulse sequences and/or using a pulse sequence with a plurality of different pulse sequence parameters.

A still further preferred embodiment of the invention is also applicable for use in logging downhole in an earth borehole. A method is set forth for determining a characteristic of oil that may be present in a downhole measurement region, including the following steps: providing a plurality of crude oil samples; determining the viscosities of the crude oil samples; performing magnetic resonance test measurements, using a predetermined operating mode, on media including said crude oil samples to obtain a set of test data; applying a plurality of test processing procedures to said set of test data to obtain a corresponding plurality of output test parameters relating to said respective plurality of test processing procedures; deriving, for said plurality of crude oil samples, a plurality of correlations, each of said correlations relating said plurality of output test parameters to the viscosities of said crude oil samples; performing downhole measurements in the measurement region with a nuclear magnetic resonance logging device, operated substantially with said predetermined operating mode, to obtain a set of logging data, and applying a measurement processing procedure, which substantially corresponds to one of said test processing procedures, to said logging data to obtain an output logging parameter; and determining the oil characteristic using said output logging parameter and a selected one of said plurality of correlations. In a form of this embodiment of the invention, the selected one of said correlations is the correlation that corresponds to said one of the plurality of test processing procedures.

Further features and advantages of the invention will become more readily apparent from the following detailed description when taken in conjunction with the accompanying drawings.

DETAILED DESCRIPTION

Figure 11:
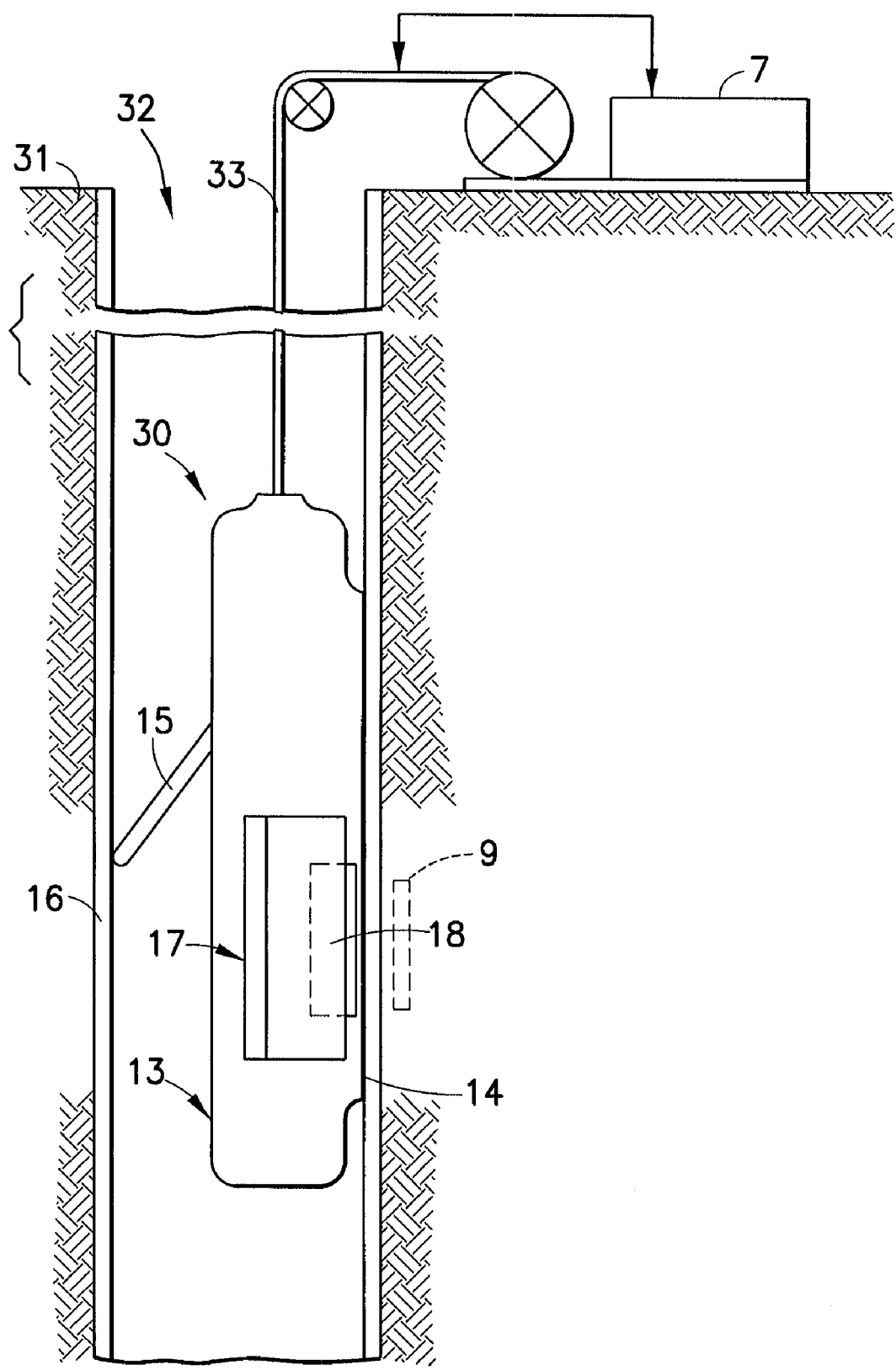
FIG. 11 is a diagram, partially in block form, of a well logging apparatus which can be used in practicing embodiments of the invention.

Referring to FIG. 11, there is shown an apparatus for investigating subsurface formations 31 traversed by a borehole 32, which can be used in practicing embodiments of the invention. The borehole 32 is typically, but not necessarily filled with a drilling fluid or mud which contains finely divided solids in suspension, and mudcake 16 is shown on the walls of the borehole A magnetic resonance investigating apparatus or logging device 30 is suspended in the borehole 32 on an armored cable 33, the length of which substantially determines the relative depth of the device 30. The length of cable 33 is controlled by suitable means at the surface such as a drum and winch mechanism (not shown). Surface equipment, represented at 7, can be of conventional type, and can include a processor subsystem and communicates with the all the downhole equipment. It will be understood that processing can be performed downhole and/or uphole, and that some of the processing may be performed at a remote location. Also, while a wireline is illustrated, alternative forms of physical support and communicating link can be used, for example in a measurement while drilling system. As described for example in the U.S. Pat. No. 5,055,787, the magnetic resonance logging device 30 has a face 14 shaped to intimately contact the borehole wall, with minimal gaps or standoff, and a retractable arm 15 which can be activated to press the body of the tool 13 against the borehole wall during a logging run, with the face 14 pressed against the wall's surface. Although the tool 13 is shown as a single body, the tool may alternatively comprise separate components such as a cartridge, sonde or skid, and the tool may be combinable with other logging tools.

The magnetic resonance logging device 30 includes a magnet array 17 and an RF antenna 18 positioned between the array 17 and the wall engaging face 14. Magnet array 17 produces a static magnetic field $B_0$ in regions surrounding the tool 13. The antenna 18 produces, at selected times, an oscillating magnetic field $B_1$ which is focussed into formation 12, and is superposed on the static field $B_0$ within those parts of formation opposite the face 14. The "volume of investigation" of the tool, shown in dashed region 9 in FIG. 11, is a vertically elongated region directly in front of tool face 14. As described in the referenced Patent, the tool 13 can make measurements by magnetically tipping the nuclear spins of particles in formation 12 with a pulse of oscillating field $B_1$, and then detecting the precession of the tipped particles in the static field $B_0$ within the volume of investigation over a period of time. Reference can also be made to Morriss, C. E., Deutch, P., Freedman, R., McKeon, D., Kleinberg, R. L., 1996, "Operating Guide for the Combinable Magnetic Resonance Tool", Log Analyst, November-December 1996, pg. 53-60.

Figure 12:
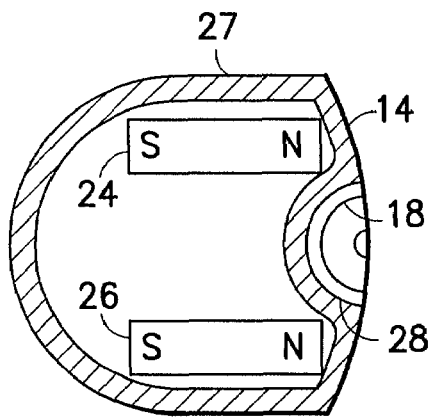
FIG. 12 is a cross-sectional diagram of a portion of the nuclear magnetic resonance logging device of FIG. 11.

FIG. 12 shows a magnet array 17 of the type disclosed in an embodiment of the referenced '787 Patent. The magnet array includes two permanent magnets 24 and 26, which are mounted generally parallel to each other within a metal alloy body 27. The body 27 should be of a material having low magnetic permeability, so as to not interfere with the static magnetic field. Magnets 24 and 26 are slabs which are elongated in the longitudinal direction of the borehole. The magnetic poles of each magnet are not on the smallest faces of the slab, commonly viewed as the ends of a bar magnet. Instead, the poles appear on the two opposing edges of the slab magnet and point to the left and right, respectively, in the Figure. Therefore, within the formation 12, the magnetic field $B_0$ surrounding the magnets remains fairly constant along the longitudinal direction of the borehole axis. In the illustration of FIG. 12, magnets 24, 26 are symmetrically mounted in the two sides of the body 27 with the north poles facing the same direction, that is, the direction of the face 14 of the tool. One or more further permanent magnets can be used.

Figure 13:
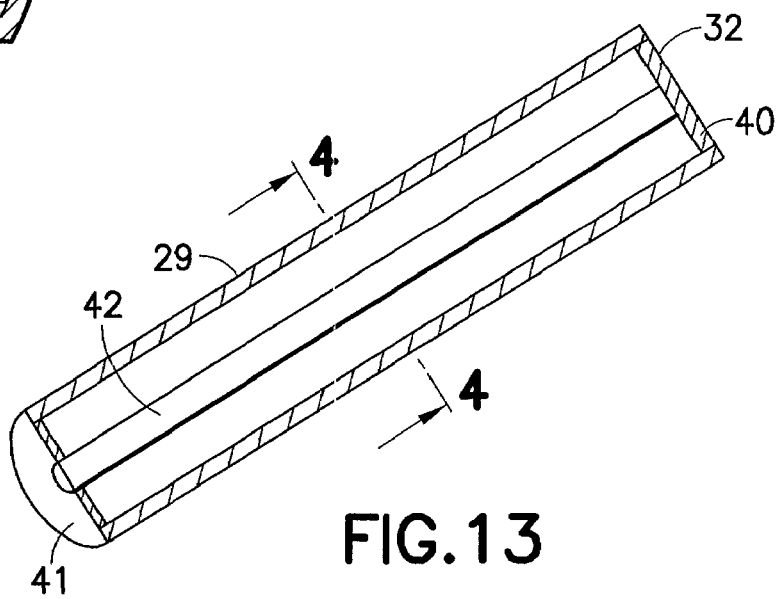
FIG. 13 is a perspective view of the RF antenna of the FIG. 11 nuclear magnetic resonance logging device.
Figure 14:
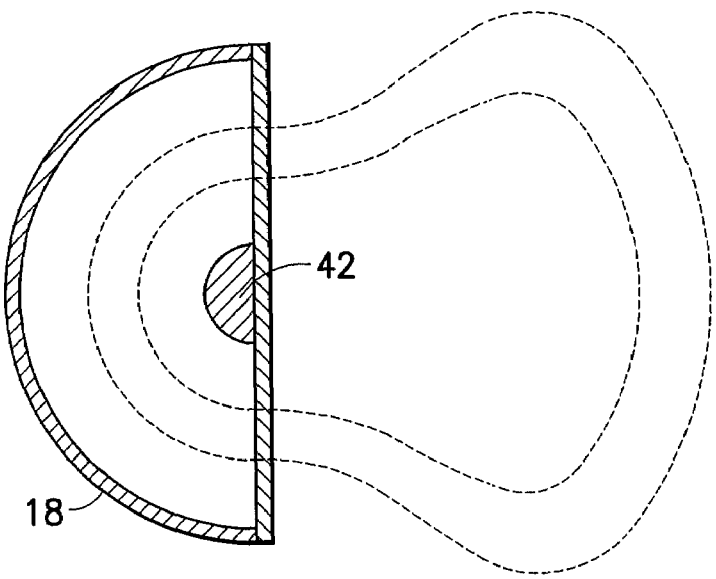
FIG. 14 is a cross-sectional view of the RF antenna of FIG. 13, as taken through a section defined by the arrows 4-4 in FIG. 13.

As described in the referenced '787 Patent, the metal body 27 has, on the front face 14 thereof, a semi-cylindrically shaped cavity or slot 28 which faces formations engaged by the face 14. The cavity 28 is adapted for receiving an RF antenna 18 that is shown in FIGS. 13 and 14. The antenna 18 is positioned outside of the metal body 27 (FIG. 12) of the tool, and is thereby shielded from electromagnetic communication with regions of the borehole which lie behind the body 27, or regions of other formations in directions intercepted by the body 27. Antenna 18 is thus responsive only to magnetic fields originating in front of the wall engaging face 14, e.g. fields originating in the formation 12 or in the mudcake or mud which contacts face 14 in the vicinity of the antennas 18. In a disclosed embodiment of the referenced Patent, the body 27 is made of metal alloy sheathing, rigidly attached to interior metal bracing, which envelops most components of the tool other than the antenna 18, including the circuitry, the magnet array 17, and the hydraulics system of the arm 15. The Patent points out that the body 27 can alternatively be constructed of other materials, so long as the overall structure is sufficiently strong and the magnetic field of the magnet array 17 can penetrate the body and enter the adjoining formation 12.

Figure 1:
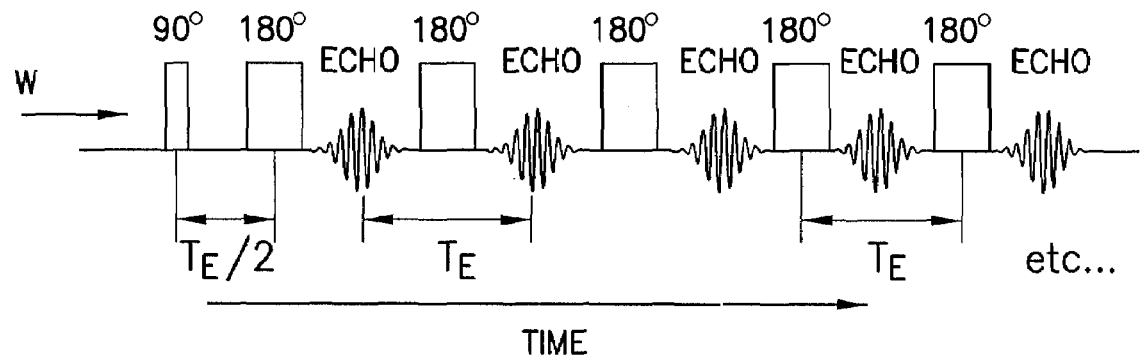
FIG. 1 illustrates a prior art Carr-Purcell-Meiboom-Gill (CPMG) pulse sequence for the measurement of T2 [Carr and Purcell, 1954; Meiboom and Gill, 1958]. When the wait time W is varied, the pulse sequence is the so-called Saturation Recovery/Carr-Purcell-Meiboom-Gill (SR/CPMG) pulse sequence, for the measurement of T1 and T2 simultaneously [see e.g. U.S. Pat. No. 5,032,551; and A. Sezginer, et al. (1991), supra].
Figure 2:
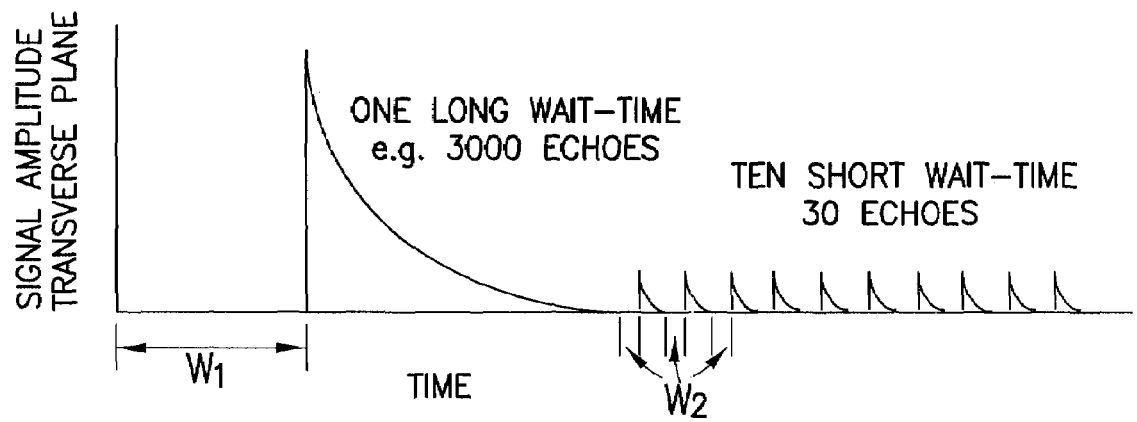
FIG. 2 illustrates the timing of a prior art so-called Enhanced Precision Mode (EPM). After a long wait time WL=W1, a single long CPMG sequence is acquired. Then, a series of short CPMG sequences is acquired with short wait time $W_S$=W2 between each. The short sequences improve the precision of the early-time magnetization decay [see D. McKeon et al. (1999), supra].
Figure 3:
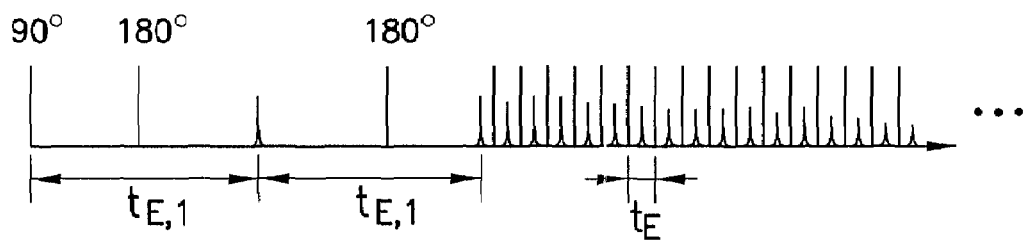
FIG. 3 illustrates the timing of a prior art so-called diffusion editing (DE) pulse sequence to measure D-T2 distribution functions [see M. D. Hurlimann et al. (2002), supra].
Figure 4:
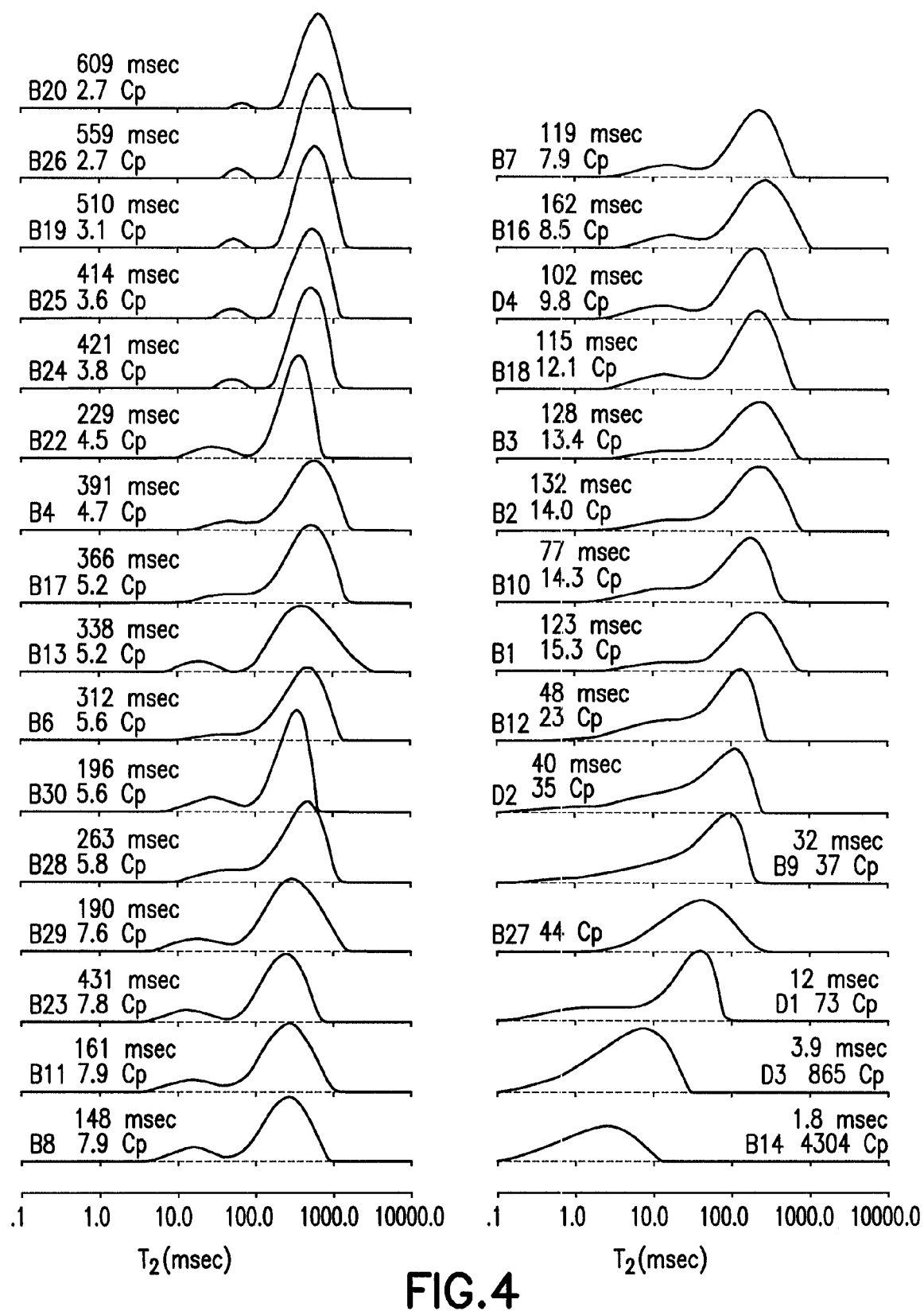
FIG. 4 illustrates tansverse relaxation time distributions of crude oils. The $T_2$-distributions for bulk oil samples from the Belridge field, California, are plotted in order of increasing viscosity, from top left to bottom right. Sample number logarithmic mean $T_2$ ($T_{2,log}$) and measured viscosity (in centipoise) are shown for each example. [see C. E. Morriss et al. (1994), supra].
Figure 5:
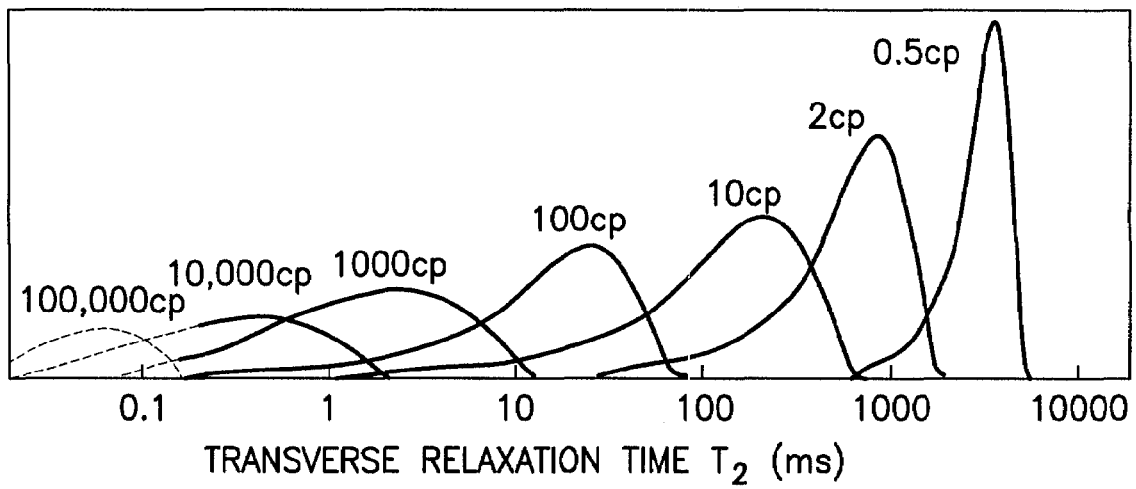
FIG. 5 is a graph of transverse relaxation time distributions for oils with a range of viscosities, as measured by NMR apparatus with a finite dead time. Only relaxation time components with T2>0.2 ms are visible; these components are represented by solid curves. Invisible components are shown as dotted curves.
Figure 6:
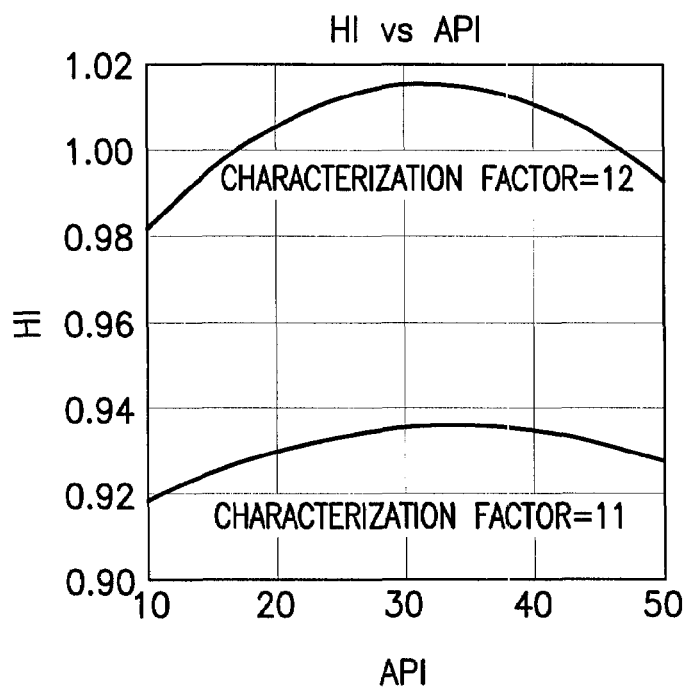
FIG. 6 is a graph showing the intrinsic hydrogen index of crude oils as a function of API gravity and characterization factor K. Oils with K=12 are predominantly pariffinic, while oils with K=11 have more aromatic content.
Figure 7A:
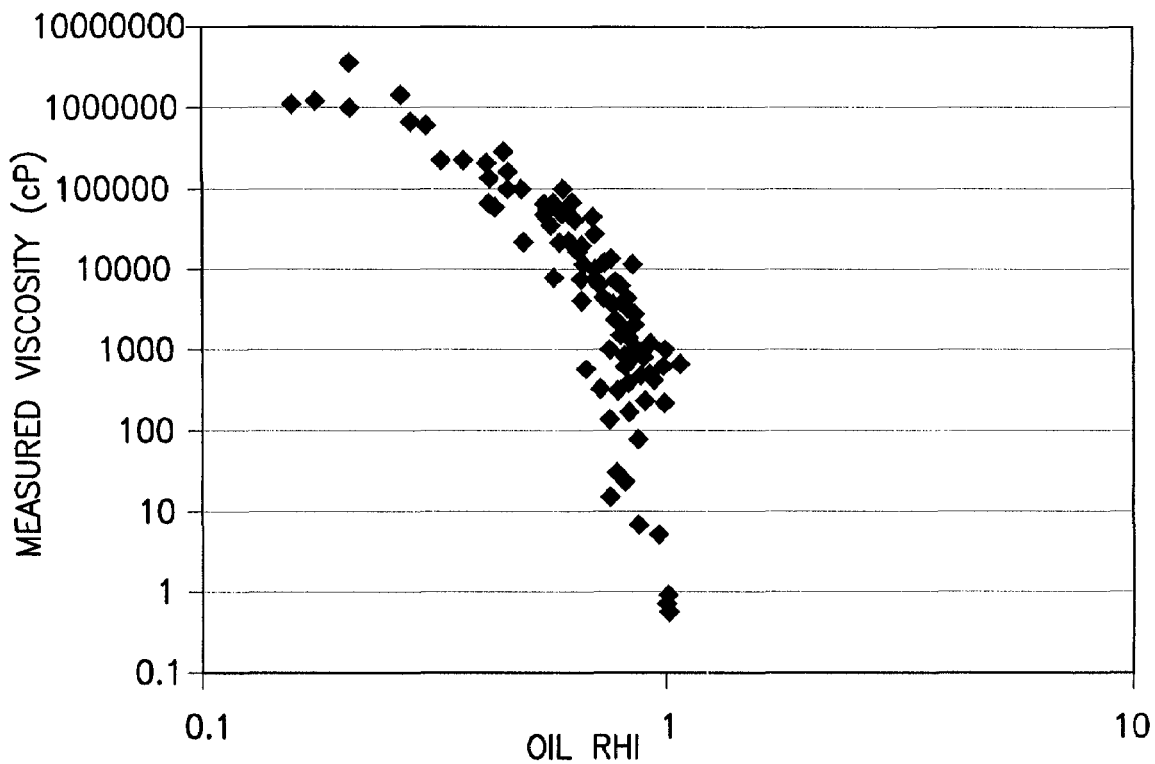
FIG. 7a is a graph of viscosity plotted against relative hydrogen index for a range of oils [see Bryan et al., 2005, supra].
Figure 7B:
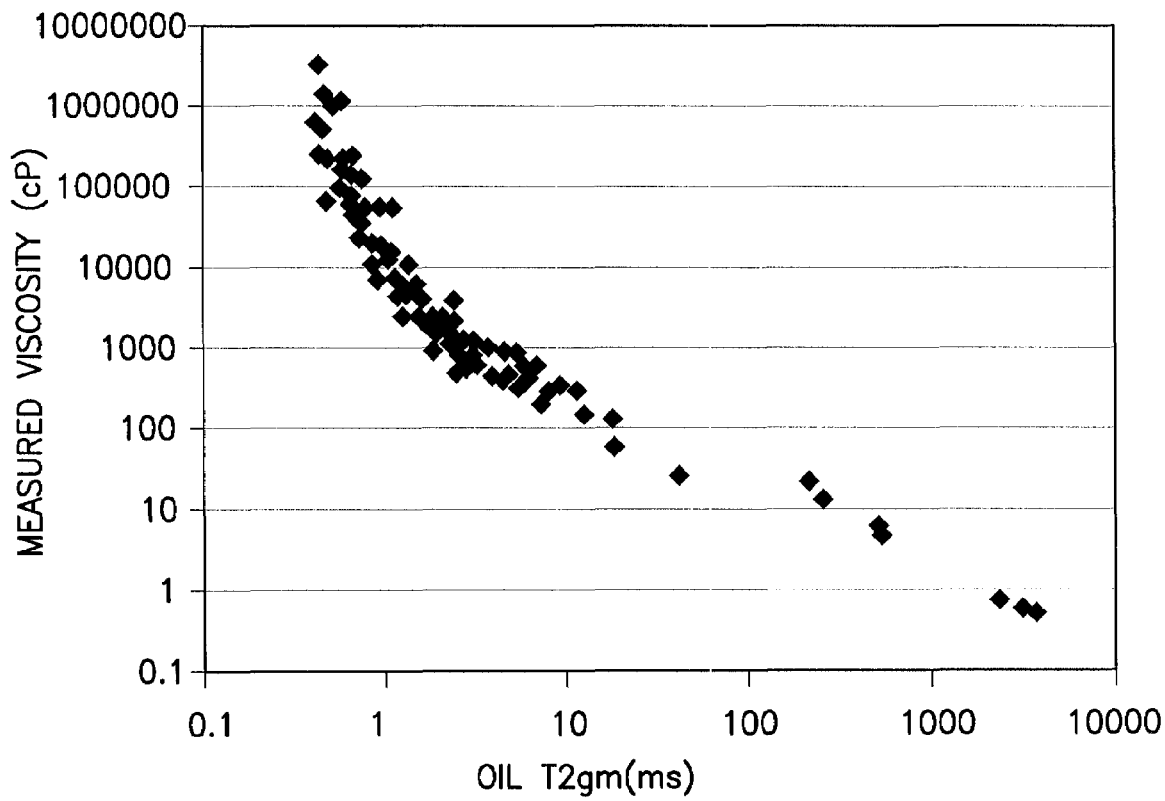
FIG. 7b is a graph of viscosity plotted against the geometric mean of the T2 distribution for a range of oils [see again Bryan et al., 2005, supra].
Figure 8:
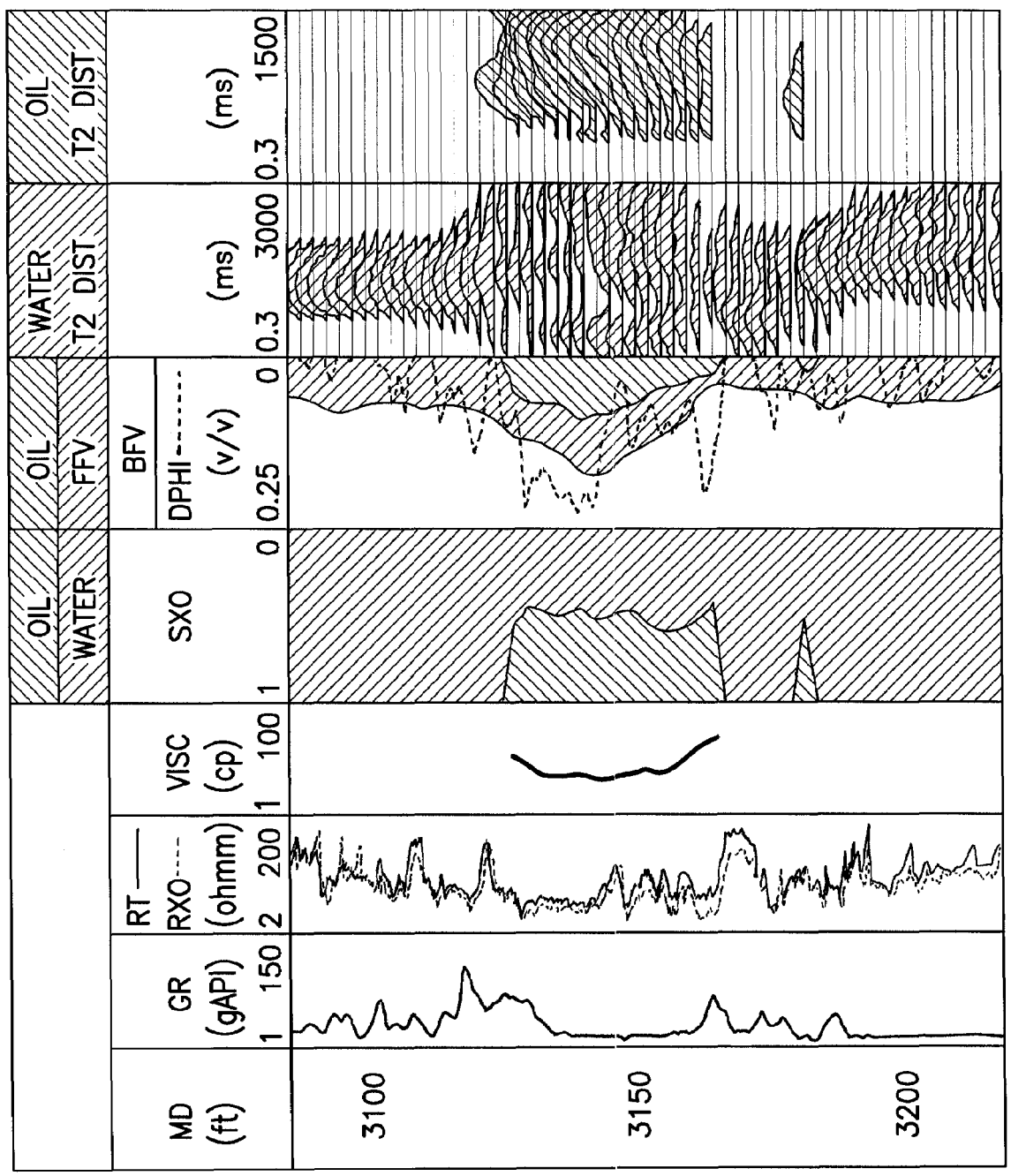
FIG. 8 is a log illustrating a prior art method for determining oil saturation and viscosity [see N. J. Heaton et al., 2002, supra].
Figure 9:
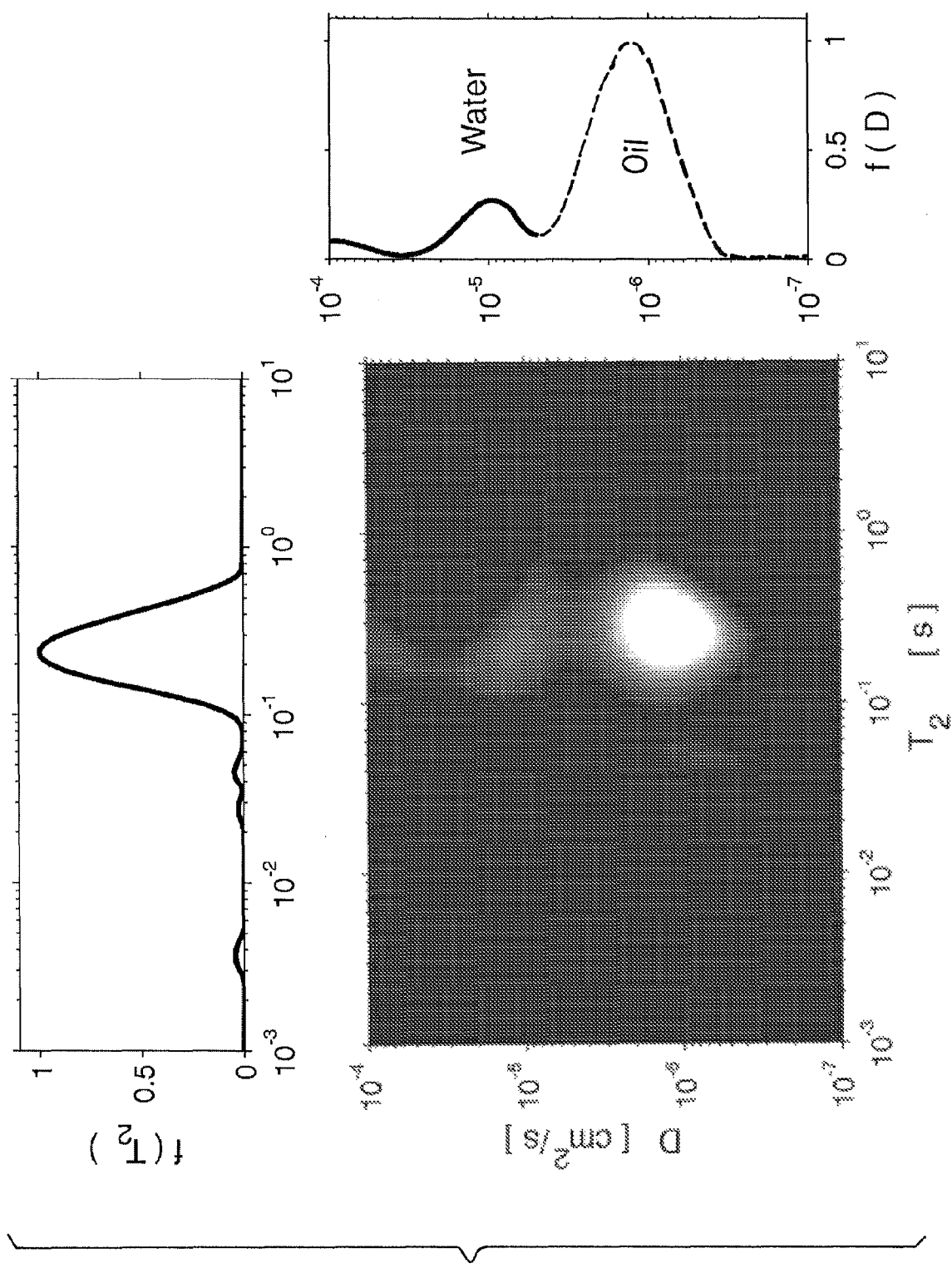
FIG. 9 shows a prior art diffusion-relaxation map for resolving oil and water NMR signals [see Hurlimann et al., 2002, supra].

In the referenced '787 Patent, the antenna 18 is used both as an RF transmitter to produce an oscillating magnetic field in the formations, and as a receiving antenna to detect coherent magnetic signals emanating from precessing protons (spins) after the oscillating field is terminated. The antenna, which has a body 29 and an elongated center probe 42, across which signals are applied and detected, serves effectively as a current loop which produces an oscillating magnetic field $B_1$ (see FIG. 4) within the volume of investigation that is perpendicular to the static magnetic field, $B_0$ (which is radial in the volume of investigation). The body 29 is trough-shaped and has end plates 40, 41 with the center conductor or probe 42 extending from one end plate 40 to the other end plate 41, parallel to and centered in the semi-cylindrical trough 29. It will be understood that various other types of magnetic resonance logging equipment can be used in practicing the invention.

The type of tool described in conjunction with FIGS. 11-14 can be modified, for faster logging, as disclosed, for example, in D. McKeon et al., "An Improved NMR Tool Design For Faster Logging", Transactions Of SPWLA, 1999. As described in that publication, the increased acquisition speed is possible because of advances in NMR technology, including longer permanent magnets and altered pulse sequences. One of the altered pulse sequences is called enhanced precision mode ("EPM"), which improves the repeatability of total porosity and bulk fluid volume measurements. The EPM measurement consists of one long wait-time pulse sequence followed by a series of short wait-time pulse sequences. The short wait-time sequences improve accuracy and precision of measurements of clay-bound water and small pore porosity. Typically, the wait time of the short pulses is 20 ms; only a few echoes are acquired for each short wait-time CPMG (typically 30 to 100). The EPM measurement reduces the porosity and bulk fluid volume measurement standard deviations. In addition, the EPM measurement improves the $T_2$ sensitivity limit of the total porosity measurement, and provides more accurate measurement of heavy oil at short $T_2$.

Figure 15A:
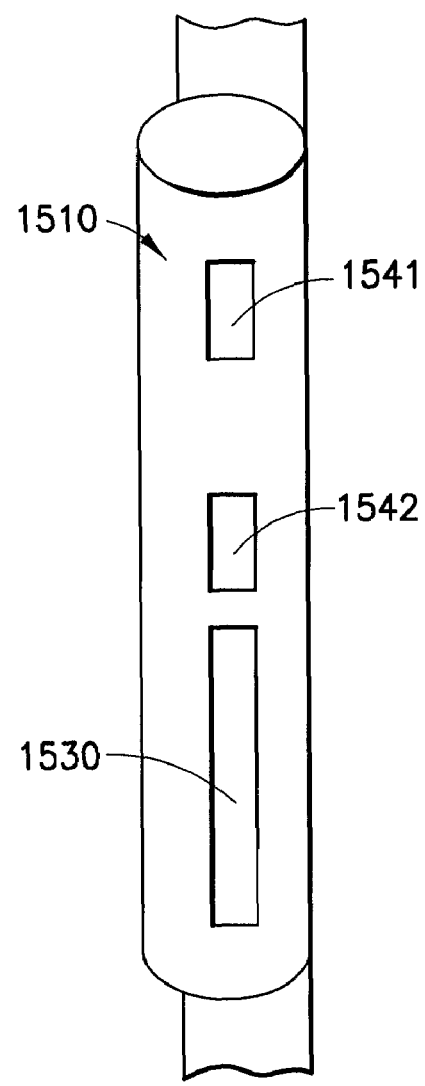
FIGS. 15a and 15b show, in simplified front perspective view and simplified cross-section, respectively, a type of NMR logging device that can operate with multiple depths of investigation.
Figure 15B:
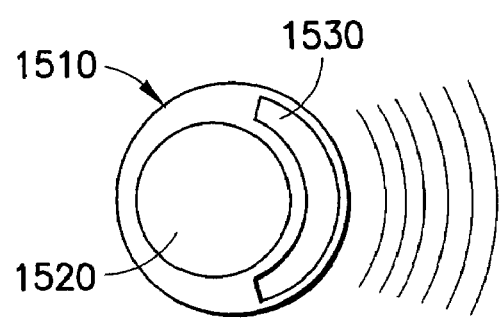

In some implementations of the invention, a measurement or measurements are taken on media in a particular measurement region (for example, in the earth formations, the borehole, or a fluid-containing vessel of a formation testing device) and the measurement or measurements are repeated, say, with the tool at a different depth level or position in the borehole. It will be understood, however, that the NMR logging device may be capable of performing measurements at, for example, plural depths of investigation. For purposes hereof, each different region of investigation (e.g. different depths of investigation or other variations), taken, for example, with an NMR tool at a particular position, such as a particular depth level, are considered to be sub-regions of the measurement region. An example of an NMR logging device that has plural depths of investigation is the "MRX" (trademark of Schlumberger) disclosed, for example, in L. DePavia et al., "A Next-Generation Wireline NMR Logging Tool" Society of Petroleum Engineers, SPE 84482, 2003. As described in that publication, the "MRX" tool 1510, shown in simplified front view in FIG. 15a, has cylindrical permanent magnet 1520, a main antenna 1530 and high resolution antennas 1541 and 1542. The main antenna 1530 operates at multiple frequencies and is intended primarily for fluid characterization applications. There are eight different frequencies of operation corresponding to independent measurement volumes (shells) with evenly spaced depths of investigation. The shell volumes form concentric arcs in front of the antenna, as illustrated in FIG. 15b. The high-resolution antennae operate at a single frequency, corresponding to a slightly shallower depth of investigation than the main antenna.

Using NMR to Estimate Viscosity

Applicant has observed that the sensitivity of NMR measurements to the details of data acquisition and processing suggest that no one NMR-viscosity correlation will be optimal for all well logs. Thus, in accordance with an aspect hereof, an NMR-viscosity correlation should be devised for each of a number of measurement programs. In an embodiment of the invention, the following procedure is used to develop program-specific NMR-viscosity correlations:

(a) Acquire a representative group of crude oil samples. In some cases, these can be live crude oils, i.e. they contain dissolved gas under pressure. If only degassed samples are available, a gas/oil ratio correction can be applied [see e.g. R. Freedman, A. Sezginer, M. Flaum, A. Matteson, S. Lo, and G. J. Hirasaki, "A New NMR Method Of Fluid Characterization In Reservoir Rocks: Experimental Confirmation And Simulation Results", SPE 63214, SPE Annual Technical Conference and Exhibition, 1-4 Oct. 2000; S.-W. Lo, G. J. Hirasaki, W. V. House, and R. Kobayashi, "Mixing Rules And Correlations Of NMR Relaxation Time With Viscosity, Diffusivity, And Gas/Oil Ratio Of Methane/Hydrocarbon Mixtures", SPE 77264, SPE Journal 7(1), 24-34 (March 2002); and G. J. Hirasaki, S.-W. Lo, and Y. Zhang, "NMR Properties Of Petroleum Reservoir Fluids", Magnetic Resonance Imaging 21, 269-277 (2003)]. It is noted, however, that the accuracy of this correction has been questioned [see Winkler et al., 2004].

(b) Measure the viscosity of each sample as a function of temperature and pressure over relevant ranges. Perferably, if possible, gas saturation of the oils is maintained to replicate downhole conditions.

(c) In the laboratory, perform NMR measurements on each sample as a function of temperature and pressure over relevant ranges. The measurements simulate the performance of a borehole logging tool with respect to pulse sequence, pulse sequence parameters, and signal-to-noise ratio. For this purpose, a laboratory NMR instrument, or the NMR borehole logging tool itself, is used.

(d) For each sample, the data is processed using the same algorithms that are applied to borehole logging data. Output data may include such parameters as the initial slope of the CPMG echo decay, the T2 distribution, the geometrical mean (logarithmic mean) relaxation time of the T2 distribution, the T1 distribution, the geometrical mean (logarithmic mean) relaxation time of the T1 distribution, the hydrogen index or relative hydrogen index, the diffusion coefficient, diffusion-relaxation maps, relaxation-relaxation maps, or any other output suitable parameters used to analyze downhole NMR logs.

(e) For each sample, auxiliary measurements reflective of other borehole logging tools can be acquired and analyzed.

(f) For each group of samples and each combination of acquisition and processing methods and parameters, a correlation is devised relating NMR and other measurements to viscosity.

There are many classes of correlations that can be developed in this fashion for the present embodiment. An example is a relatively simple class of correlations generated by developing equations that relate viscosity to combinations of simple log outputs, such as that described by prior art Equation (14). Similar correlations can be constructed with hydrogen index and T1. The geometrical mean relaxation time is only one of several ways of characterizing a relaxation time distribution; others include the mode, median, and arithmetic mean of the distribution. Any of these may be used singly or in combination to produce an NMR-viscosity correlation.

Figure 16:
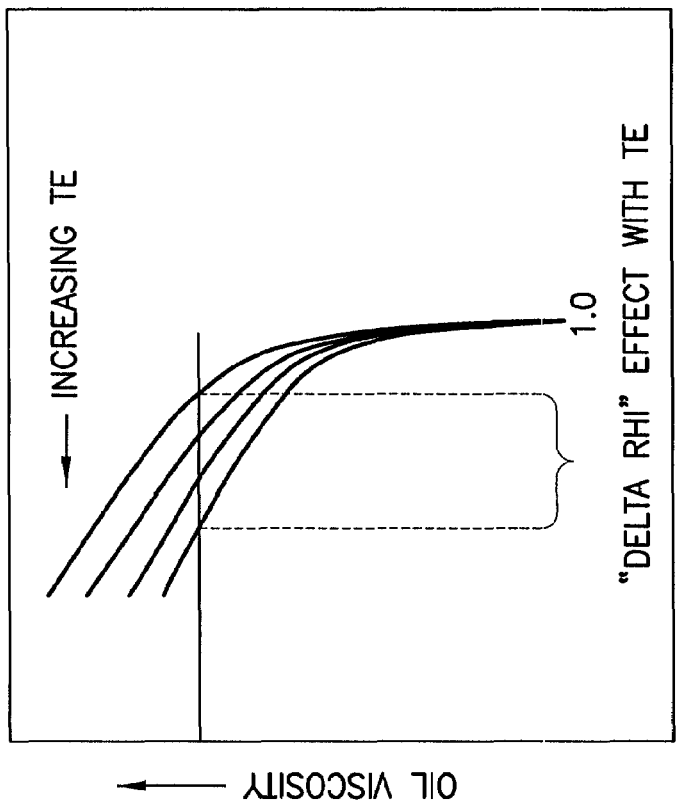
FIG. 16 shows graphs illustrating on the left, the effect of increasing $T_E$ on oil $T_{2LM}$, and, on the right, effect of increasing $T_E$ on oil hydrogen index or relative hydrogen index.
Figure 16:
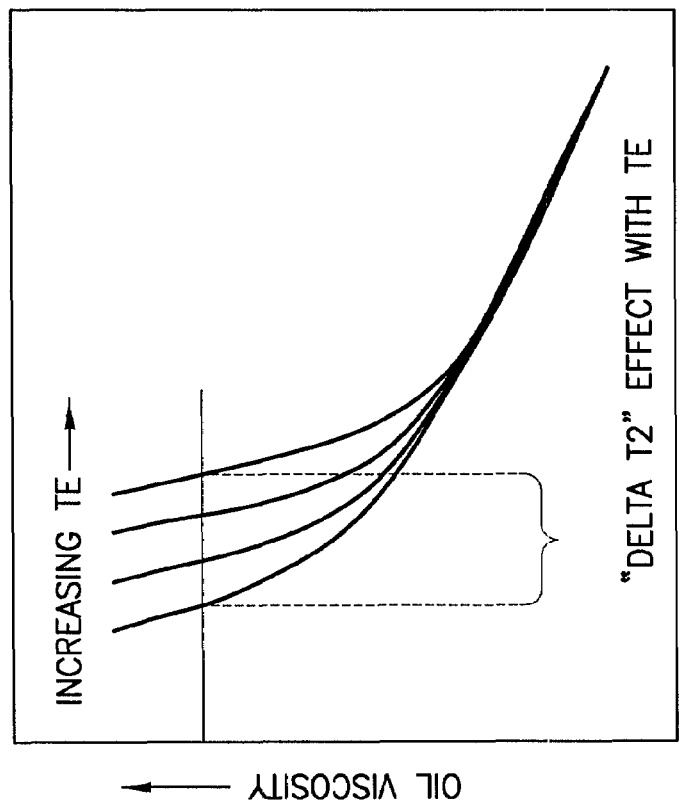

A more complex class of correlations is based on the change of apparent NMR properties as a function of NMR pulse sequence parameters. For example, for a given oil viscosity η, the $T_{2LM}$ and RHI may be unique functions of $T_E$, as illustrated in FIG. 16. In FIG. 16, the graph on the left shows the effect of increasing $T_E$ on oil $T_{2LM}$, and graph on the right shows the effect of increasing $T_E$ on oil hydrogen index or relative hydrogen index.

Figures 17, 18:
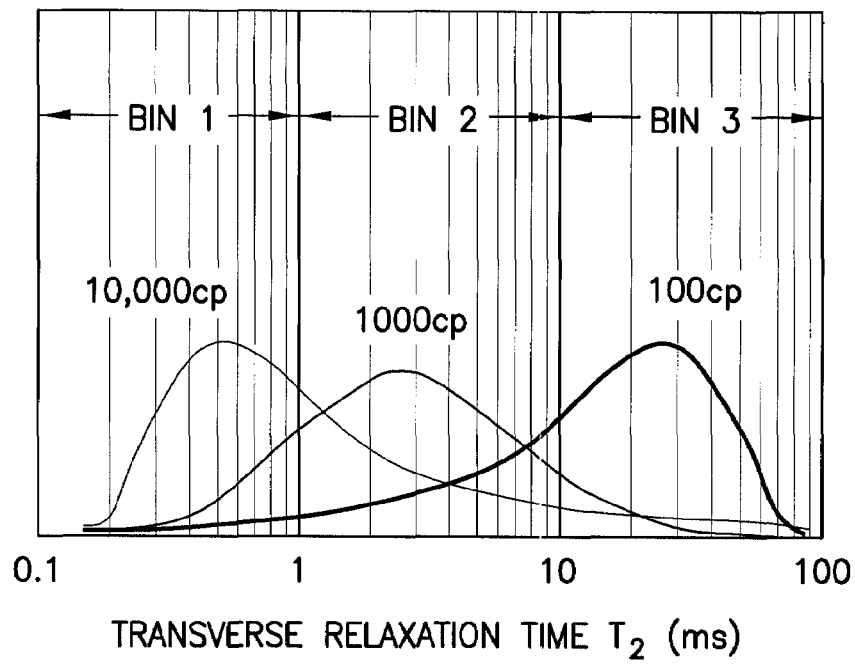
FIG. 17 shows graphs that illustrate relaxation time distributions for three hypothetical crude oils. Although oils with different viscosities may span the same range in the T2 distribution, they may have very different weights in specific bins, e.g. 0.1-1 ms, 1-10 ms, and 10-100 ms in this example.
FIG. 18 is a Table showing $(T_E)_{min}$, gradient (G), and $G_{max} \cdot (T_E)_{min}$ for several existing MNR borehole logging tools.

Yet another class of correlations relates viscosity to the weights of various parts of the relaxation time distribution, as illustrated in FIG. 17. As one example, viscosity can be correlated with the relative amounts of signal found in various ranges of relaxation time ("bins"), e.g. 0.1-1 ms, 1-10 ms, and 10-100 ms, for Bin 1, Bin 2, and Bin 3, respectively, in the example of FIG. 16.

Yet another class of correlations uses time-domain NMR data. For example, the initial slope of the CPMG echo decay can be expected to be correlated with viscosity, with steeper slopes being associated with higher viscosities.

The foregoing classes of correlations are exemplary, and it will be understood that others can be used.

Certain efficiencies can be achieved in the implementation of embodiments hereof. For example, when it is desired to minimize the time and expense of NMR laboratory work, the measurement program can be streamlined for efficiency. It is often possible to use a single data set for multiple purposes. For example, it may be desired to obtain NMR-viscosity correlations for echo spacings $T_E$=0.2 ms and $T_E$=0.6 ms, and for signal-to-noise ratios of S/N=20 and S/N=5. The data necessary to develop the four desired NMR-viscosity correlations can be obtained by measuring each crude oil sample, at each desired temperature and pressure, four times. However this procedure is relatively time consuming and demanding of laboratory resources. To save time and resources, each sample can be measured once, at each temperature and pressure, using the minimum echo spacing and the maximum signal-to-noise ratio. For the above example, data sets may be acquired with $T_E$=0.2 ms and S/N=20. In a pre-processing step, $T_E$=0.6 ms data can be simulated by a 3:1 decimation of the original echo train, and S/N=5 data can be simulated by adding zero-mean Gaussian noise of the appropriate amplitude to the original and decimated echo trains.

When a T1-related quantity (e.g. $T_{1LM}$ or other characteristic of the T1 distribution) is used in a correlation, molecular diffusion in magnetic field gradients has no effect, because T1 is not affected by diffusion. However, T2-related quantities can be affected by diffusion. When the diffusion contribution to the relaxation rate is not negligible, long $T_E$ data cannot be simulated by simply decimating short $T_E$ data, as described in the previous section. Echo train decimation to simulate long $T_E$ data is only appropriate when diffusion does not significantly contribute to T2 relaxation. In order for diffusion to be negligible, the following condition must hold:

$$\frac{1}{T_{2LM}} \gg \frac{1}{T_{2D}} \qquad (15)$$

where $T_{2LM}$ is the logarithmic mean transverse relaxation time of the oil in the absence of magnetic field gradients and $$\frac{1}{T_{2D}} = \frac{1}{12}(\gamma G T_E)^2 D \qquad (16)$$

$1/T_{2D}$ is the additive contribution to the transverse relaxation rate due to diffusion, $\gamma=2.675\times10^4$ Gauss$^{-1}$s$^{-1}$ is the gyromagnetic ratio of hydrogen, G is the magnetic field gradient (either applied by the measurement apparatus or internal to rock), and D is the fluid diffusion coefficient. Each logging tool has a unique magnetic field gradient profile. The ranges of field gradients for several existing borehole logging tools, listed as tool #1 through tool #8, are listed in Table 1 of FIG. 18.

An established relationship between diffusion coefficient D and viscosity η is $$D = \frac{bT}{\eta} \qquad (17)$$

where T is the absolute (Kelvin) temperature and b=5.05× 10$^{-8}$ cm$^2$·cp/s·K [see e.g. R. Freedman, N. Heaton, and M. Flaum, "Field Applications Of A New Nuclear Magnetic Resonance Fluid Characterization Method", SPE Reservoir Evaluation and Engineering, December 2002, pg 455-464]. For oils with viscosity below about 200 cp, in the absence of magnetic field gradients, $$\frac{1}{T_{2LM}} = \frac{\eta}{a \cdot T} \qquad (18)$$

where a=0.004 cp·s/K [again, see Freedman et al., 2002, supra]. Then Eqn (15) reduces to $$\eta \gg \left(\frac{a \cdot b}{12}\right)^{1/2} \cdot \gamma \cdot T \cdot G \cdot T_E \qquad (19)$$

$$\eta \gg \left(0.110 \frac{cp \cdot cm}{G \cdot s \cdot K}\right) \cdot T \cdot G \cdot T_E \qquad (20)$$

A typical heavy oil reservoir temperature is 60° C., which is T=333 K. Table 1 lists Gmax·$(T_E)$min for various borehole NMR tools run at their respective minimum echo spacings. The largest value in the table is Gmax·$(T_E)$min=0.02 with $(T_E)$min=0.45 ms, so a 4:1 decimation ($T_E$=1.8 ms) is valid for η≫3 cp.

Figure 10:
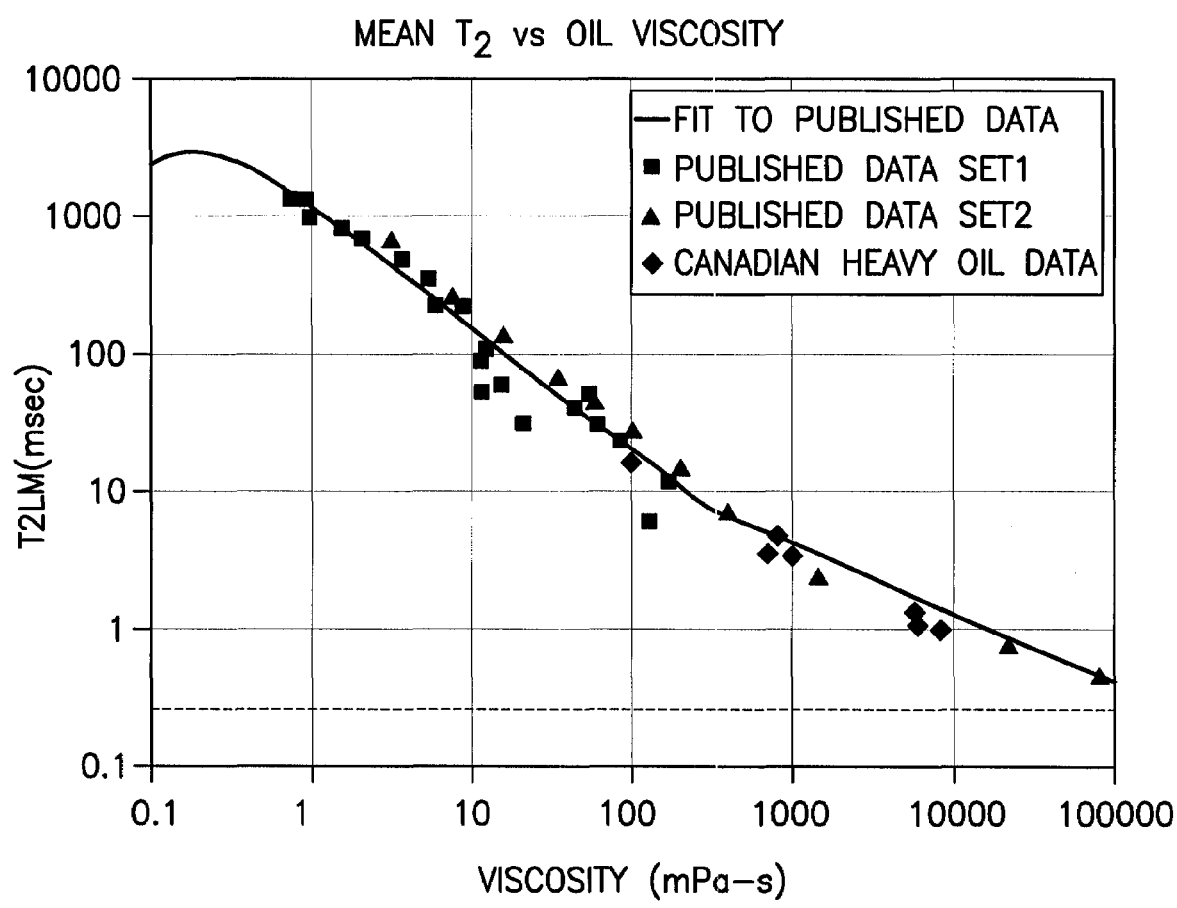
FIG. 10 is a graph showing an example of viscosity with NMR logarithmic mean $T_2$.

The relaxation time of oils at laboratory temperature, over the entire viscosity range shown in FIG. 10, and in the absence of magnetic field gradients, can be approximated by $$\frac{1}{T_{2LM}} = \frac{\eta^{3/4}}{(1.0 \, cp^{3/4} s)} \qquad (21)$$

Use of this data set does not materially alter the conclusion that, for heavy oils, the relaxation time effect of molecular diffusion in the gradients of currently deployed borehole logging tools is not significant, and that therefore the decimation technique is appropriate for improving the efficiency of the laboratory measurement program.

If diffusion relaxation is non-negligible for one or more oils as measured by a particular logging tool, a pre-processing correction can be implemented. The correction is based on the correlation between diffusion coefficient and bulk (G=0) relaxation time, both of which depend on viscosity.

Next, wait times will be treated. The wait time controls the overall NMR signal amplitude from a sample through the sample's longitudinal relaxation time, T1. The sample is fully polarized if it is exposed to the static magnetic field for a time at least as long as 5×T1 before pulsing begins, or between successive pulse sequences. Thus, for highest accuracy, it is desirable to use a wait time at least five times longer than the T1 of the slowest relaxing (longest T1) component of the longitudinal relaxation time distribution.

Some pulse sequences, such as the above-referenced Enhanced Precision Mode (EPM) and the Magnetic Resonance Fluid mode (MRF), employ variable wait times, Wi [McKeon et al., 1999, supra; Heaton et al., 2002, supra]. To simulate these sequences, it is prudent to make laboratory measurements with all the wait times used by the borehole tool.

Figure 19:
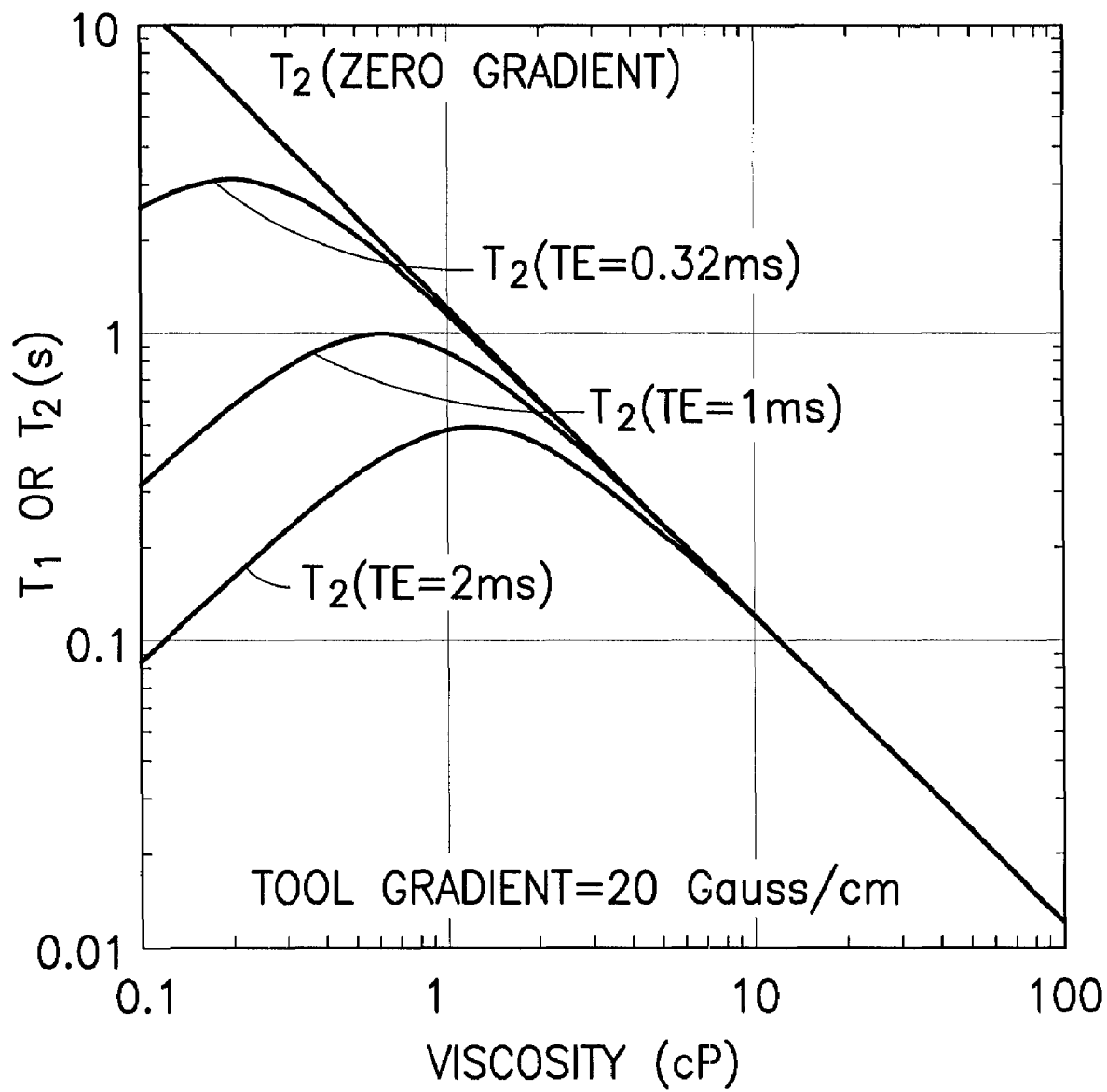
FIG. 19 is a graph showing prior art average values $T_{2LM}$ for many crude oils. The parabolic curves at low viscosity represent the effect of diffusion in magnetic field gradients on the T2 measurement, assuming the mode of an NMR tool gradient distribution, as described in R. L. Kleinberg and H. J. Vinegar, 1996, supra, for various values of echo spacing.

If all wait times Wi are more than five times longer than the slowest relaxing component of the T1 distribution, measurements at only one of the wait times is required. The EPM sequence typically employs a short wait time of $W_S=20$ ms. Only the heaviest of crude oils have T1<4 ms (see FIG. 19). Thus, except for the heaviest oils, if an NMR-viscosity correlation for the EPM sequence is desired, laboratory measurements should be made with both $W_S$ and $W_L$.

In the well log analysis of heavy oil reservoirs, the NMR signal is usually comprised of oil and water components. Water and oil signals often overlap in both the time domain raw data (echoes) and in the processed data (T1 distributions or T2 distributions). A recent technique [see J. Seccombe, R. Akkurt, M. Smith, and R. J. M. Bonnie, "Ranking Oil Viscosity In Heavy Oil Reservoirs" SPWLA 46th Annual Logging Symposium, 26-29 Jun. 2005] uses the entire T1 distribution to estimate oil viscosity. To the extent that the T1 distribution includes both water and oil signals, this procedure may lead to significant errors in the estimation of oil viscosity. Applicant asserts that, when oil and water signals overlap, it is preferable to separate them before applying NMR-viscosity correlations. The procedures used to decompose oil and water signals can influence the form of NMR-viscosity correlations.

Figure 20:
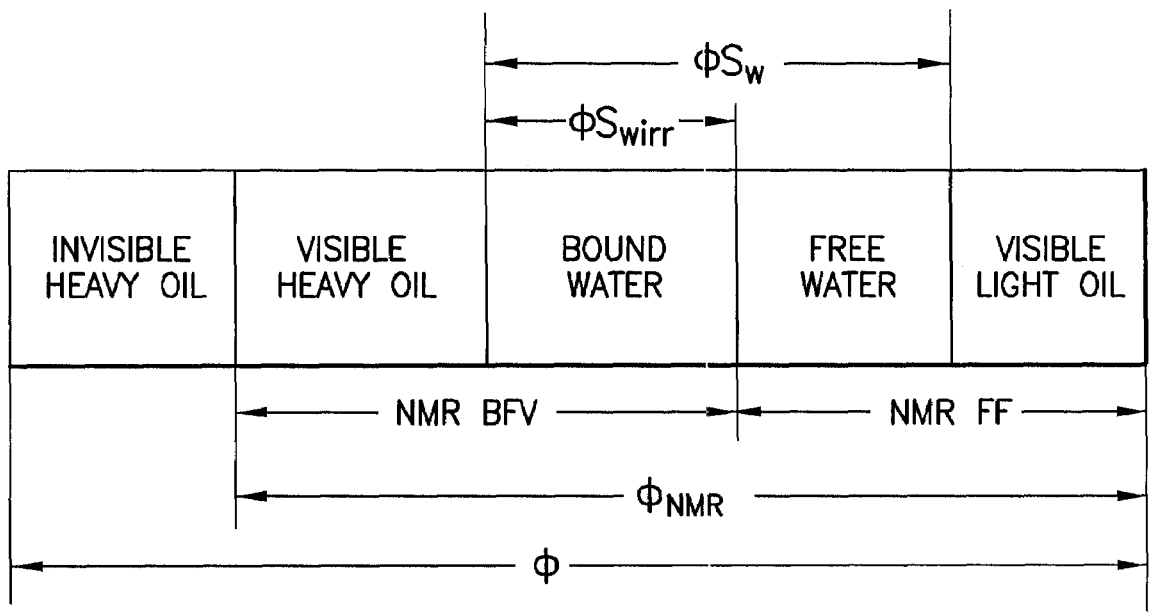
FIG. 20 illustrates a porosity model defining invisible heavy oil, visible heavy oil, and visible light oil fractions of a crude oil mixed with water in an earth formation.

One method that has been found useful to separate overlapping water and oil signals in heavy and light oil reservoirs is based on the porosity model shown in FIG. 20, and uses the following steps:

(a) Determine the true porosity $\phi$, which can be found from any or all of the following logs: density, density-neutron cross plot, acoustic, etc. The preferred method for finding $\phi$ is a multivariate analysis, which takes into account several measurements in a consistent manner.

(b) The total water volume is the true porosity times water saturation, $\phi Sw$. The water saturation when both water and oil are present can be estimated from Archie's Law $$S_w = \left(\frac{aR_w}{R_t \phi^m}\right)^{1/n} \quad (22)$$

where Rw is the resistivity of the pore water, Rt is the measured deep ("true") formation resistivity, and a, m and n are empirically determined constants, which are adjusted to give Sw=1 in 100% water-saturated formations. Water saturation can also be estimated from dielectric logging, which is relatively insensitive to water resistivity Rw. Total water volume is composed of movable (free) water, and bound (irreducible) water, $\phi Sw=\phi Swf+\phi Swirr$.

(c) The bound water volume, $\phi Swirr$, is found from any of a number of borehole measurements. The gamma ray (GR) log can be employed, using a calibration in which bound water volume equals total water volume when the water saturation is irreducible, i.e. at maximum oil saturation, or in shales. Other measurements are useful if it is known that the formation is at irreducible water saturation. These include the dielectric, Rxo, density-neutron cross-plot, or capture sigma logs. The preferred method for finding Swirr is a multivariate analysis that takes into account several measurements in a consistent manner.

(d) The movable water volume is total water in excess of bound water, $\phi Swf=\phi Sw-\phi Swirr$.

(e) The total oil volume is found from the total water volume, $\phi So=\phi-\phi Sw$.

(f) The invisible heavy oil is the difference between true porosity and NMR porosity, $\phi Soi=\phi-\phi NMR$. This assumes there is no NMR-invisible water. In clean formations (those with little or no clay or shale content), most NMR tools detect all formation water. However, not all NMR borehole logging tools are capable of measuring the total water signal in shales and shaly sands. Tools having that capability make measurements with a short echo spacing TE and a good signal to noise ratio [see, for example, R. Freedman, A. Boyd, G. Gubelin, D. McKeon and C. E. Morriss, "Measurement Of Total NMR Porosity Adds New Value To NMR Logging", SPWLA 38th Annual Logging Symposium, Jun. 15-18, 1997].

(g) NMR porosity is divided into NMR free fluid (FF) and NMR bound fluid volume (BFV), $\phi NMR=BFV+FF$, by using a cutoff value (e.g. T2cut=33 ms), by using a tapered cutoff method [see R. L. Kleinberg and A. Boyd, "Tapered Cutoffs For Magnetic Resonance Bound Water Volume", Society of Petroleum Engineers Paper 38737 (1997)], or by any other method.

(h) The visible heavy oil volume is the excess of NMR bound fluid over the irreducible water volume, $\phi Sovh=BFV-\phi Swirr$.

(i) The visible light oil volume is the excess of NMR free fluid over free water, $\phi Sovl=FF-\phi Swf$.

The use of internally consistent multivariate volumetric estimators is helpful in deriving accurate results for the water and oil volumes.

The results of this water-oil decomposition method are the invisible oil volume, $\phi Soi$, the visible heavy oil volume, $\phi Sovh$, and visible light oil volume $\phi Sovl$, which sum to the total oil volume $\phi So$. These three oil volumes can be determined by laboratory measurements on bulk oil samples in the absence of rock and water. For any particular oil, the three ratios Soi/So, Sovh/So, and Sovl/So can be used to develop an NMR-viscosity correlation. Generally speaking, as oil viscosity increases, Soi/So increases and Sovl/So decreases. These oil saturation ratios depend on the details of data acquisition and processing methods and parameters. Thus the NMR measurements used to create the database must simulate the operation of the borehole logging tools in order to create useful NMR-viscosity correlations.

What is claimed is:

1. For use in logging downhole in an earth borehole, a method for determining a characteristic of oil that may be present in a downhole measurement region, comprising the steps of:

providing a plurality of crude oil samples;

determining the viscosities of the plurality of crude oil samples;

performing nuclear magnetic resonance test measurements, using a predetermined operating mode having operating parameters impacting relaxation time and hydrogen index measures of the plurality of crude oil samples, on media including said plurality of crude oil samples to obtain test data;

applying a test processing procedure to said test data to obtain an output test parameter relating to said test data and said predetermined operating mode;

deriving, for said plurality of crude oil samples, a correlation relating said output test parameter to the viscosities of said crude oil samples;

performing downhole measurements in the measurement region with a nuclear magnetic resonance logging device, operated with substantially said predetermined operating mode, to obtain logging data, and applying a measurement processing procedure to said logging data to obtain an output logging parameter; and determining the oil characteristic using said output logging parameter and said correlation.

2. The method as defined by claim 1, wherein said characteristic of oil comprises the viscosity of oil in the measurement region.

3. The method as defined by claim 1, wherein said characteristic of oil comprises the distribution of viscosities of crude oil components in the measurement region.

4. The method as defined by claim 1, wherein said characteristic of oil comprises oil volume in the measurement region.

5. The method as defined by claim 1, wherein said characteristic of oil comprises oil saturation in the measurement region.

6. The method as defined by claim 1, wherein said characteristic of oil comprises light oil volume and/or heavy oil volume in the measurement region.

7. The method as defined by claim 1, wherein said characteristic of oil comprises light oil saturation and/or heavy oil saturation in the measurement region.

8. The method as defined by claim 1, wherein said step of performing test measurements comprises simulating measurements by the logging device used to perform downhole measurements.

9. The method as defined by claim 1, wherein said step of performing test measurements comprises performing said measurements with the logging device used to perform downhole measurements.

10. The method as defined by claim 1, wherein said step of performing nuclear magnetic resonance test measurements using a predetermined operating mode having operating parameters impacting relaxation time and hydrogen index measures of the plurality of crude oil samples comprises performing said nuclear magnetic resonance test measurements using a predetermined pulse sequence with predetermined pulse sequence parameters.

11. The method as defined by claim 1, wherein said step of performing nuclear magnetic resonance test measurements using predetermined operating mode having operating parameters impacting relaxation time and hydrogen index measures of the plurality of crude oil samples comprises performing said nuclear magnetic resonance test measurements using a predetermined signal-to-noise ratio.

12. The method as defined by claim 1, wherein said measurement processing procedure substantially corresponds to said test processing procedure.

13. The method as defined by claim 1, further comprising:

performing further nuclear magnetic resonance test measurements, using a further operating mode, on media including said plurality of crude oil samples to obtain further test data;

applying said test processing procedure to said further test data to obtain a further output test parameter relating to said test data and said predetermined operating mode;

deriving, for said plurality of crude oil samples, a further correlation relating said further output test parameter to the viscosities of said plurality of crude oil samples;

performing downhole measurements in the measurement region with a nuclear magnetic resonance logging device, operated with substantially said further operating mode, to obtain further logging data, and applying said measurement processing procedure to said further logging data to obtain a further output logging parameter; and determining an oil characteristic using said further output logging parameter and said further correlation.

14. For use in logging downhole in an earth borehole, a method for determining a characteristic of oil that may be present in a downhole measurement region, comprising the steps of:

providing a plurality of crude oil samples;

determining the viscosities of the plurality of crude oil samples;

performing nuclear magnetic resonance test measurements, using a plurality of operating modes having operating parameters impacting relaxation time and hydrogen index measures of the plurality of crude oil samples, on media including said plurality of crude oil samples to obtain a corresponding plurality of sets of test data;

applying a test processing procedure to each of said plurality of sets of test data to obtain a corresponding plurality of output test parameters relating to said respective plurality of operating modes;

deriving, for said plurality of crude oil samples, a plurality of correlations, each of said correlations relating said plurality of output test parameters to the viscosities of said plurality of crude oil samples;

performing downhole measurements in the measurement region with a nuclear magnetic resonance logging device, operated substantially with one of said plurality of operating modes, to obtain a set of logging data, and applying a measurement processing procedure to said logging data to obtain an output logging parameter; and determining the oil characteristic using said output logging parameter and a selected one of said plurality of correlations.

15. The method as defined by claim 14, wherein said selected one of said correlations is the correlation that corresponds to said one of said plurality of operating modes.

16. The method as defined by claim 14, wherein said characteristic of oil comprises the viscosity of oil in the measurement region.

17. The method as defined by claim 14, wherein said characteristic of oil comprises the distribution of viscosities of crude oil components in the measurement region.

18. The method as defined by claim 14, wherein said step of performing nuclear magnetic resonance test measurements comprises simulating measurements by the nuclear magnetic resonance logging device used to perform downhole measurements.

19. The method as defined by claim 14, wherein said step of performing test measurements comprises performing said measurements with the nuclear magnetic resonance logging device used to perform downhole measurements.

20. The method as defined by claim 14, wherein said step of performing nuclear magnetic resonance test measurements using a plurality of operating modes having operating parameters impacting relaxation time and hydrogen index measures of the plurality of crude oil samples comprises performing said nuclear magnetic resonance test measurements using a plurality of different pulse sequences.

21. The method as defined by claim 14, wherein said step of performing nuclear magnetic resonance test measurements using a plurality of operating modes having operating parameters impacting relaxation time and hydrogen index measures of the plurality of crude oil samples comprises performing said nuclear magnetic resonance test measurements using a pulse sequence with a plurality of different pulse sequence parameters.

22. The method as defined by claim 21, wherein said different pulse sequence parameters comprise different echo spacing times.

23. The method as defined by claim 22, wherein at least one of said different echo spacing times is implemented using decimation.

24. For use in logging downhole in an earth borehole, a method for determining a characteristic of oil that may be present in a downhole measurement region, comprising the steps of:

providing a plurality of crude oil samples;

determining the viscosities of the crude oil samples;

performing nuclear magnetic resonance test measurements, using a predetermined operating mode having operating parameters impacting relaxation time and hydrogen index measures of the plurality of crude oil samples, on media including said crude oil samples to obtain a set of test data;

applying a plurality of test processing procedures to said set of test data to obtain a corresponding plurality of output test parameters relating to said respective plurality of test processing procedures;

deriving, for said plurality of crude oil samples, a plurality of correlations, each of said correlations relating said plurality of output test parameters to the viscosities of said crude oil samples;

performing downhole measurements in the measurement region with a nuclear magnetic resonance logging device, operated substantially with said predetermined operating mode, to obtain a set of logging data, and applying a measurement processing procedure, which substantially corresponds to one of said test processing procedures, to said logging data to obtain an output logging parameter; and determining the oil characteristic using said output logging parameter and a selected one of said plurality of correlations.

25. The method as defined by claim 24, wherein said selected one of said correlations is the correlation that corresponds to said one of said plurality of test processing procedures.

26. The method as defined by claim 24, wherein said characteristic of oil comprises the viscosity of oil in the measurement region.

27. The method as defined by claim 25, wherein said characteristic of oil comprises the distribution of viscosities of crude oil components in the measurement region.

28. The method as defined by claim 24, wherein said step of performing nuclear magnetic resonance test measurements comprises simulating measurements by the nuclear magnetic resonance logging device used to perform downhole measurements.

29. The method as defined by claim 24, wherein said step of performing test measurements having operating parameters impacting relaxation time and hydrogen index measures of the plurality of crude oil samples comprises performing said measurements with the nuclear magnetic resonance logging device used to perform downhole measurements.

30. The method as defined by claim 24, wherein said step of applying a plurality of test processing procedures to said set of test data comprises applying a plurality of different processing algorithms to said set of test data.

* * * * *